US00RE49351E

(19) United States
(12) Reissued Patent
Honda et al.

(10) Patent Number: US RE49,351 E
(45) **Date of Reissued Patent: *Jan. 3, 2023**

(54) CYTOPROTECTIVE AGENT

(71) Applicant: Biogen MA Inc., Cambridge, MA (US)

(72) Inventors: Kazuo Honda, Tokyo (JP); Terumasa Hashimoto, Tokyo (JP); Keita Shibata, Tokyo (JP); Keiko Hasegawa, Tokyo (JP); Keiji Hasumi, Tokyo (JP)

(73) Assignee: Biogen MA Inc., Cambridge, MA (US)

( * ) Notice: This patent is subject to a terminal disclaimer.

(21) Appl. No.: 16/584,521

(22) Filed: Sep. 26, 2019

Related U.S. Patent Documents

Reissue of:
(64) Patent No.: 9,078,880
Issued: Jul. 14, 2015
Appl. No.: 13/381,995
PCT Filed: Feb. 5, 2010
PCT No.: PCT/JP2010/051711
§ 371 (c)(1),
(2) Date: Jan. 3, 2012
PCT Pub. No.: WO2011/004620
PCT Pub. Date: Jan. 13, 2011

U.S. Applications:
(63) Continuation of application No. 15/496,256, filed on Apr. 25, 2017, now Pat. No. Re. 47,684, which is an application for the reissue of Pat. No. 9,078,880.

(30) Foreign Application Priority Data

Jul. 6, 2009 (JP) ..... 2009-160278

(51) Int. Cl.
*A61K 31/407* (2006.01)
*C07D 491/04* (2006.01)

(52) U.S. Cl.
CPC ..... *A61K 31/407* (2013.01); *C07D 491/04* (2013.01)

(58) Field of Classification Search
CPC ..... A61K 31/407; C07D 491/04; A61P 9/10; A61P 7/02; A61P 43/00
See application file for complete search history.

(56) References Cited

U.S. PATENT DOCUMENTS

| | | | | |
|---|---|---|---|---|
| 7,361,493 | B1 | 4/2008 | Hammond et al. | |
| RE47,684 | E * | 11/2019 | Kazuo | C07D 491/04 |
| 2008/0293799 | A1 | 11/2008 | Hasumi et al. | |
| 2009/0216028 | A1 | 8/2009 | Hasumi et al. | |

FOREIGN PATENT DOCUMENTS

| | | | |
|---|---|---|---|
| CN | 101346471 | | 1/2009 |
| CN | 101346471 | A | 1/2009 |
| JP | 2002-065288 | A | 3/2002 |
| JP | 2004-224737 | A | 8/2004 |
| JP | 2004-224738 | | 8/2004 |
| JP | 2004224737 | | 8/2004 |
| JP | 2004224738 | | 8/2004 |
| JP | 2008-201688 | A | 9/2008 |
| JP | 2009-132724 | A | 6/2009 |
| JP | 2009-215216 | A | 9/2009 |
| WO | 2004/002488 | A1 | 1/2004 |
| WO | 2007/040082 | | 4/2007 |
| WO | WO 2007/094071 | A | 8/2007 |
| WO | 2007/111203 | | 10/2007 |

OTHER PUBLICATIONS

Partridge, "Building a Better Clot-Buster: rt-PA and Combination Therapy," Psychiatric Therapy, Jan. 1, 2007 (Year: 2007).*
Gravanis et al., "tPA as a therapeutic target in stroke," Expert Opin. Ther. Targets, 12(2), Feb. 2008. (Year: 2008).*
Adams et al. (May 2007) "Guidelines for the Early Management of Adults with Ischemic Stroke", Stroke, pp. 1655-1711.
Adams et al (1996) "Guidelines for Thrombolytic Therapy for Acute Stroke: A Supplement to the Guidelines for the Management of Patients With Acute Ischemic Stroke, A Statement for Healthcare Professionals From a Special Writing Group of the Stroke Council, American Heart Association," Circulation, 94, pp. 1167-1174.
Adibhatla et al., Jun. 2008, "Tissue Plasminogen Activator (tPA) and Matrix Metalloproteinases in the Pathogenesis of Stroke: Therapeutic Strategies", CNS Neurol Disord Drug Targets, 7(3), pp. 243-253.
Benakis et al., 2009, "Inflammation and stroke", Kardiovaskuläre Medizin, 12(5), pp. 143-150.
Cheng et al., Jan. 2004, "Neuroprotection for Ischemic Stroke: Two Decades of Success and Failure", The Journal of the American Society for Experimental NeuroTherapeutics, vol. 1, pp. 36-45.
Cuadrado et al., Jul. 2008, "Tissue plasminogen activator (t-PA) promotes neutrophil degranulation and MMP-9 release", Journal of Leukocyte Biology, vol. 84, pp. 207-214.

(Continued)

*Primary Examiner* — Alan D Diamond
(74) *Attorney, Agent, or Firm* — Troutman Pepper Hamilton Sanders LLP

(57) ABSTRACT

Disclosed is a cytoprotective agent for use with respect to ischemic damage, including as an active ingredient a triprenyl phenol compound represented by the following general formula (I), wherein X is —CHY—C$(CH_3)_2$Z, Y and Z are each independently —H or —OH, or jointly form a single bond, and R represents a hydrogen atom or a substituent with a molecular weight of 1000 or less.

(I)

12 Claims, 5 Drawing Sheets

Specification includes a Sequence Listing.

(56) References Cited

OTHER PUBLICATIONS

Donnan, Geoffrey A., Jan. 2008, "A New Road Map for Neuroprotection", The 2007 Feinberg Lecture, pp. 242-248.
English translation of JP 2002-65288 A (Year: 2002).
English translation of JP 2004-224737 A (Year: 2004).
Hu et al. (2000) "Activation of Fibrinolysis by SMTP-7 and -8, Novel Staplabin Analogs with a Pseudosymmetric Structure," The Journal of antibiotics, vol. 53, No. 3, Mar. 2000, pp. 241-247.
Internet Stroke Center on the Wayback Machine http//:www.strokecenter.org.80/pat/ais.thm, "About Stroke", copyright 1997-2002.
Nozawa et al. (1997) "Stachybotrin C and Parvisporin, Novel Neurotogenic Compounds I. Taxonomy, Isolation, Physicochemical and Biological Properties, The Journal of Antibiotics," vol. 50, No. 8, (1997), pp. 635-640.
Sacchetti, Maria Luisa, Jun. 2008, "Is It Time to Definitely Abandon Neuroprotection in Acute Ischemic Stroke", Stroke, pp. 1659-1660.
Terr (2001) "Stachybotrys: relevance to human disease," Annals of Allergy, Asthma and Immunology, Dec. 2001, vol. 87, pp. 57-62.
USPTO translator's translation of paragraphs 0038 and 0039 of JP 2004-224737, Aug. 2004.
Longa et al., "Reversible Middle Cerebral Artery Occulsion Without Craniectomy in Rats", Stroke, 1989, vol. 20, No. 1, pp. 84-91.
Kito et al., "Experimental thromboembolic stroke in cynomoigus monkey", Journal of Neuroscience Methods, 2001; vol. 105, pp. 45-53.
Chinese Patent Office Action for Chinese Appln. Serial No. 201080030009.7, dated Jan. 14, 2013, 10 pages—English.
EP. Pat. Appln. Serial No. 10796931.3, European Search Report dated Nov. 2, 2012, 6 pages—English.
Kilic et al., "Aggravation Of focal cerebral Ischemia by tissue plasminogen activator is reversed by 3-hydroxy-3-methylglutaryl coenzyme a reductase Inhibitor but does not depend on endothelial No synthase", Stroke, vol. 36, No. 2, Feb. 2005, pp. 332-336.
Maeda et al., "A combined treatment with tacrolimus (FK506) and recombinant tissue plasminogen activator for thrombotic focal cerebral ischemia in rats: Increased neuroprotective efficacy and extended therapeutic time window", Journal of Cerebral Blood Flow and Metabolism, vol. 22, No. 10, Oct. 2002, pp. 1205-1211.
PCT/JP2010/051711, Written Opinion of IPEA dated filed Feb. 15, 2011, 6 pages—Japanese; 7 pages—English, Cert. of Trans.
PCT/JP2010/051711, International Search Report, dated Mar. 23, 2010, 2 pgs.—Japanese; 2 pgs.—English.
Kano et al. "Hemorrhagic transformation after fibrinolytic therapy with tissue plasminogen activator in a rat thromboembolic model of stroke", Brain Research, 2000, vol. 854, pp. 245-248.
Takayasu et al., "Enhancement of fibrin binding and activation of plasminogen by staplabin through induction of a conformational change in plasminogen", FEBS Letters, 1997, vol. 418, pp. 58-62.
Huang et al., "Development and Validation of Oxygen Radical Absorbance Capacity Assay for Lipophillic Antioxidants Using Randomly Methylated [beta]-Cyclodextrin as a Solubility Enhancer", Journal of Agricultural and Food Chemistry, 2002, vol. 50, No. 7, pp. 1815-1821.
Kohyama et al., "SMTP-1 and-2, Novel Analogs of Staplabin Produced by Stachybotrys Micraspora", The Journal of Antibiotics, 1997, vol. 50, No. 2, pp. 172-174.
Hasumi et al.," Isolation of SMTP-3, 4, 5 and-6 Novel Analogs of Staplabin and their Effects on Plasminogen Activation and Fibrinolysis", The Journal of Antibiotics, vol. 51, No. 12, 1998, pp. 1059-1068.
Shinohara et al., "Staplabin, a Novel Fungal Triprenyl Phenol which stimulates the Binding of Plasminogen to Fibrin and U937 Cells", The Journal of Antibiotics, 1996, vol. 49, No. 10, pp. 961-966.
Nakagawara et al., "Treatment strategy for Acute Stage Cerebral Stroke Thrombolytic Therapy for Cardiogenic Cerebral Embolism", Medicina, 2000, vol. 37, No. 7, pp. 1114-1116.
Yoneda et al., "Feature Article: Treatment of Acute Stage Cerebral infarction Drug Therapy in Acute Stage"; Geriatric Medicine, 1998, vol. 36, No. 5, pp. 679-684.
Hacks et al., Randomised double blind placebo controlled trial of thrombolytic therapy with intravenous alteplase in acute ischaemic stroke: (ECASS II), The Lancet, vol. 352, Oct. 17, 1998, pp. 1245-1251.
Matsumoto et al., "Soluble Epoxide Hydrolase as an Anti-Inflammatory Target of the Thrombolytic Stroke Drug SMTP-7", The Journal of Biological Chemistry, 2014, vol. 289, No. 52, pp. 35826-35838.
Donnan et al., "Stroke", The Lancet, 2008, vol. 371, pp. 1612-1623.
Ito et al., "SMTP-7, a new thrombolytic agent, decreases hemorrhagic transformation after transient middle cerebral artery occulusion under warfarin anticoagulation in mice", Brain Research, 2014, vol. 1578, pp. 38-48.
Types of Stroke, last reviewed on Oct. 23, 2012, available at http:www.strokeassociation.org/STROKEORG/AboutStroke/TypesofStroke/Types-of-Stroke_UCM_308531_SubHomePage.jsp.
Lansberg et al., "Efficacy and safety of tissue plasminogen activator 3 to 4.5 hours after acute ischemic stroke: a meta-analysis", Stroke, 2009, vol. 40, No. 7, pp. 2438-2441.
Shibata et al., "Evaluation of the effects of a new series of SMTPs in the acetic acid-induced embolic cerebral infarct mouse model", European Journal of Pharmacology, 2018, vol. 818, pp. 221-227.
International Search Report and Written Opinion issued in PCT/IB2020/061485 dated Jan. 26, 2021.
International Search Report and Written Opinion issued in PCT/JP2020/044574 dated Jan. 26, 2021 (English Translation of Written Opinion unavailable).
PCT/JP2010/051711, Preliminary Amendment , dated Feb. 15, 2011, 5 pgs.—Japanese; 6 pgs.—English, Cert. of Trans.
PCT/JP2010/051711, Notification Concerning Publication, dated Jan. 13, 2011—1 page.
PCT/JP2010/051711, Notification of Priority Document Submission, dated Mar. 24, 2010—1 page.
PCT/JP2010/051711, International Search Report dated Mar. 15, 2010, 2 pgs.—Japanese; 2 pgs.—English.
PCT/JP2010/051711, Amendment under PCT Article 34, 3 pgs.
Brain Research, www.esevier.com, 2000 Elsevier Science B.V., "Hemorrhagic transformation after fibrinolytic therapy with tissue plasminogen activator in a rat thromboembolic model of stroke"; Kano, Katayama, Tejima, Lo, dated Oct. 26, 1999; pp. 245-248.
1997 Federation of European Biochemical Societies, "Enhancement of fibrin binding and activation of plasminogen by staplabin through induction of a conformational change in plasminogen"; Takayasu, Hasumi, Shinohara, Endo, dated Aug. 13, 1997, pp. 58-62.
Journal of Agricultural and Food Chemistry, 2002 American Chemical Society, published on web Feb. 8, 2002: "Development and Validation of Oxygen Radical Absorbance Capacity Assay for Lipophilic Antioxidants Using Randomly Methylated Cyclodextrin as a Solubility Enhancer"; Huang, Ou, Woodill, Flanagan, Deemer, pp. 1815-1821.
The Journal of Antibiotics, Feb. 1997, "SMTP-1 and -2, Novel Analogs of Staplabin Produced by *Stachybotrys microspora*", Kohyama, Hasumi, Hamanaka, Endo, publ. Sep. 11, 1996, pp. 172-174.
The Journal of Antibiotics, vol. 51, No. 12, Dec. 1998, "SMTP-1 and -2, Novel Analogs of Staplabin, and Their Effects on Plasminogen Activation and Febriaolysis"; Hasumi, Ohyama, Kohyama, Ohsaki, Takayasu, Endo, publ Jul. 21, 1998, pp. 1059-1068.
The Journal of Antibiotics, vol. 53, No. 3, Mar. 2000, "Activation of Febrinolysis by SMTP-7 and -8, Novel Staplabin Analogs with a Pseudosymmetric Structure"; Hu, Ohyama, Hasumi, pub. Nov. 11, 1999, pp. 241-247.
The Journal of Antibiotics. vol. 49, No. 10, "Staplabin, a Novel Fungal Triprenyl Phenol which stimulates the Binding of Plasminogen to Fibrin and U937 Cells"; Shinohara, Hasumi, Hatsumi, Endo, pub. Mar. 21, 1996, 6 pgs.
Geriatric Medicine, vol. 36, No. 5, pp. 679-684 (May 20, 1998), "Feature Article: Treatment of Acute Stage Cerebral Infarction Drug Therapy in Acute Stage"; Yoneda, Mori.
American Stroke Assn., http://stroke.ahajournals.org (Sep. 20, 2011); "Efficacy and Safety of Tissue Plasminogen Activator 3 to 4.5 Hours After Acute Ischemic Stroke: A Metaanalysis"; Lansberg, Bluhmki, Thijs, publ. May 28, 2009, 5 pgs.

(56) References Cited

OTHER PUBLICATIONS

The Lancet, vol. 363, Mar. 6, 2004, www.thelancet.com, "Association of outcome with early stoke treatment; pooled analysis of Atlantis, ECASS, and NINDS rt-PA stroke trials"; pp. 768-774.
The Lancet, vol. 352, Oct. 17, 1998, "Randomised double-blind placebo-controlled trial of thrombolytic therapy with intravenouss alteplase in acute ischaemic stroke" (ECASS II), Hacke, Kaste, et al., pp. 1245-1251.
Maeda Masashi, et al.—"A combined . . . window", Journal of Cerebral Blood Flow and Metabolism, vol. 22, No. 10, Oct. 2002, pp. 1205-1211.

* cited by examiner

CYTOPROTECTIVE AGENT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application *is a continuation reissue application of U.S. patent application Ser. No. 15/496,256, filed Apr. 25, 2017, now U.S. Pat. No. RE47,684, issued Nov. 5, 2019. This application and U.S. patent application Ser. No. 15/496,256 are applications for reissue of U.S. Pat. No. 9,078,880, issued Jul. 14, 2015, from U.S. patent application Ser. No. 13/381,995, each of which* relates to and claims priority from Japanese Patent Application Serial No. JP 2009-160278 filed Jul. 6, 2009[. This application additionally relates to and claims priority from] *and* PCT Patent Application Serial No. PCT/JP2010/051711 filed Feb. 5, 2010, the entire contents of which, including sequence listing, is also incorporated herein by reference.

TECHNICAL FIELD

The present invention relates to a cytoprotective agent.

BACKGROUND ART

Ischemic damage is understood as pathosis including any and all symptoms caused by a restricted blood flow at any part of the body, wherein cells are necrotized by energy depletion in an ischemic region, so that the region falls into dysfunction. As a method of treatment for a case that the ischemia is caused by a thrombus, the development of a thrombolytic drug and a thrombolytic drug therapy using the same has been pursued with an object of lysing the thrombus to recover the blood supply to the ischemic region.

For example, a thrombolytic drug of alteplase (recombinant DNA tissue plasminogen activator, rt-PA) has been developed focusing attention on the action of the plasminogen activator (t-PA). According to Brain Res., 2000; 854: 245-248, alteplase activates plasminogen to plasmin, and the plasmin degrades fibrin, which constitutes a nucleus to generate a thrombus.

Further, SMTP (Stachybotrys microspora triprenyl phenol) compounds are a group of compounds having a triprenyl phenol skeleton produced by a filamentous bacterium, and are known to have a thrombolysis promotion action or a vascularization inhibitory action according to Japanese Patent Laid-Open No. 2004-224737, Japanese Patent Laid-Open No. 2004-224738, and WO2007/111203. With respect to the thrombolysis promotion action, an action mechanism is indicated by FEBS Letter, 1997; 418: 58-62, that an SMTP compound causes a change in the conformation of plasminogen resulting in increasing the sensitivity of the plasminogen to t-PA and the binding of the plasminogen onto a thrombus etc. so as to promote lysis of the thrombus.

SUMMARY OF INVENTION

Technical Problem

When a thrombus is removed by administration of a thrombolytic drug and a blood flow is restored in a region having lapsed into ischemia, there arises a problem of so-called ischemia reperfusion damage. In the brain, for example, cerebral edema may be augmented, or intracranial hemorrhage may take place. Consequently, the development of a drug having a cytoprotective action to reduce the risk of various cell damages caused by ischemia, especially the risk of ischemia reperfusion damage is important.

While concerning an SMTP compound, since it has a plasminogen activation action, it has been presumed that it would exhibit a thrombolysis promotion action, but it has not been known yet about other effects of the same on ischemic damage.

In view of the foregoing, the present invention aims to provide a cytoprotective agent with superior effectiveness in inhibiting dysfunction caused by ischemia, as well as a novel use of a triprenyl phenol compound as a drug.

Solution to Problem

An aspect of the present invention is a cytoprotective agent for use with respect to ischemic damage comprising as an active ingredient a triprenyl phenol compound represented by the following general formula (I).

(I)

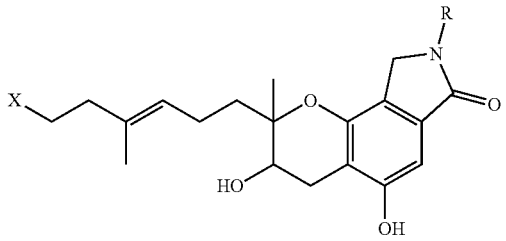

In the general formula (I), X is —CHY—$C(CH_3)_2Z$, Y and Z are each independently —H or —OH, or jointly form a single bond, and R represents a hydrogen atom or a substituent with a molecular weight of 1000 or less.

Specific examples of the triprenyl phenol compound represented by the general formula (I), wherein the R is a substituent with a molecular weight of 1000 or less include a triprenyl phenol compound represented by the following general formula (II) or (III).

(II)

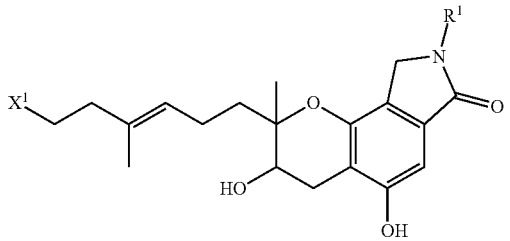

(III)

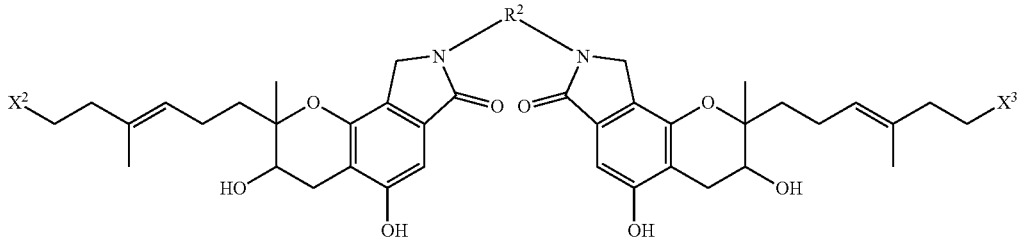

In the general formula (II) or (III), $X^1$, $X^2$ and $X^3$ are each independently —CHY—$C(CH_3)_2Z$; Y and Z are each independently —H or —OH, or jointly form a single bond; $R^1$ represents any one among the following (A) through (D):

(A) a residue of an amino compound selected from the group consisting of a natural amino acid, a D-isomer of a natural amino acid, and a compound derived by substituting a carboxy group in a natural amino acid or a D-isomer of a natural amino acid by a hydrogen atom, a hydroxy group, or a hydroxymethyl group, from which one amino group has been removed (provided that —$(CH)_2$—OH is excluded);

(B) an aromatic group having at least one selected from the group consisting of a carboxy group, a hydroxy group, a sulfonic group and a secondary amino group as a substituent or a part of a substituent, or an aromatic group that contains a secondary amino group and may contain a nitrogen atom;

(C) an aromatic amino acid residue represented by the following formula (II-1);

(II-1)

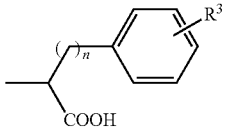

In the formula (II-1), $R^3$ is a substituent, which may be present or absent, representing at least one substituent selected from the group consisting of a hydroxy group, a carboxy group, and a C1 to C5 alkyl group, and n represents an integer of 0 or 1; or (D) a substituent represented by $-L^1-L^2-R^4$, wherein $L^1$ represents a linking group comprising a C1 to C4 alkylene group having a carboxy group, $L^2$ represents a linking group expressed by —NH—C(═O)— or —NH—C(═S)—NH—, and $R^4$ represents a 9-fluorenylalkyloxy group having a C1 to C3 alkyloxy group, or a polyheterocyclic group represented by the following formula (II-2), (II-2)

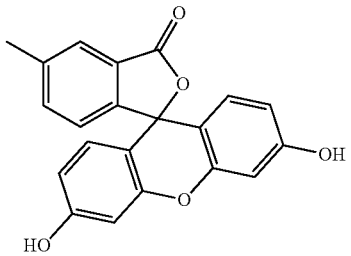

and $R^2$ represents a residue of an amino compound selected from the group consisting of a natural amino acid with two amino groups, a D-isomer of a natural amino acid with two amino groups, a compound derived by substituting a carboxy group in a natural amino acid with two amino groups or a D-isomer of a natural amino acid with two amino groups by a hydrogen atom, a hydroxy group, or a hydroxymethyl group, compounds represented by $H_2N$—CH(COOH)—$(CH_2)_n$—$NH_2$ (n being an integer from 0 to 9), and compounds represented by $H_2N$—CH(COOH)—$(CH_2)_m$—$S_p$—$(CH_2)_q$—CH(COOH)—$NH_2$ (m, p and q each independently being an integer from 0 to 9), from which two amino groups have been removed.

With respect to a cytoprotective agent according to the present invention, ischemic damage is preferably thrombosis (including thromboembolism; hereinafter the same shall apply). Further with respect to the cytoprotective agent according to the present invention, ischemic damage is more preferably cerebral infarction.

Advantageous Effects of Invention

According to the present invention, a cytoprotective agent having superior effectiveness in inhibiting dysfunction caused by ischemia, as well as a novel use of a triprenyl phenol compound as a drug, can be provided.

DESCRIPTION OF EMBODIMENTS

Figure 1:
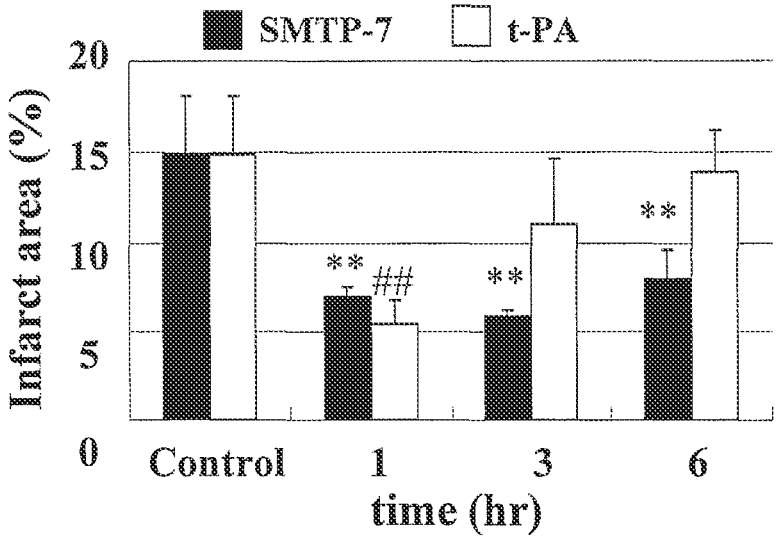
FIG. 1 is a diagram showing the percentage of a cerebral infarction area in Example 2 according to the present invention.

A cytoprotective agent according to the present invention will be described below in more detail. A numerical range expressed herein by "a to b" means a range inclusive of the a and the b as the minimum value and the maximum value.

A cytoprotective agent according to the present invention contains a triprenyl phenol compound represented by the general formula (I) as an active ingredient and is used against ischemic damage.

A triprenyl phenol compound represented by the general formula (I) according to the present invention, (hereinafter occasionally referred to as "a triprenyl phenol compound according to the present invention") protects cells from being damaged by ischemic damage and inhibits dysfunction caused by the ischemia, although the specific action and mechanism thereof have not yet been clarified.

In this regard, "ischemic damage" is generally understood as a pathosis including any and all symptoms caused by restricted blood flow at any part of the body. Namely, it is understood that cells are damaged by energy depletion in an ischemic region, or cells are damaged after the recovery of the blood flow (ischemia reperfusion damage) on the occasion of ischemic damage, whereby the region lapses into dysfunction. According to the present invention, the triprenyl phenol compound is thought to effectively inhibit ischemia reperfusion damage. In this respect, the above action is different from resuming the blood flow to the ischemic region and restoring the energy supply by promoting lysis of a thrombus, thereby inhibiting cell damage.

Further, "dysfunction caused by ischemia" herein includes any and all symptoms expressed as a result of restricted blood flow at any part of the body.

"Inhibition of dysfunction" is a concept that also includes "improvement of dysfunction", and the effectiveness thereof can be evaluated by the size of a damaged region and the severity of a symptom of a particular disease. For example, with respect to brain dysfunction, the effectiveness can be evaluated by the size of a damaged brain area or the size of an edema recognized by CT, MRI, cerebral angiography, or the like, or the effectiveness can be evaluated by an indicator, such as neurological symptom, impairment of activity of daily living, motor paralysis, or the like, that appeared as a symptom. Further, the effectiveness can be evaluated by the degree of increase of interleukin-1β (IL-1β), tumor necrosis factor-α (TNF-α), interleukin-6 (IL-6), or the like, the expression of which is enhanced by inflammation of tissues.

In order to effectively exert the function of a cytoprotective agent according to the present invention, it is effective to use it with respect to thrombosis, which is one type of ischemic damage. Generally, thrombosis is understood as a state in which blood is solidified intravascularly. Specific examples of a pathosis or a disease include transient ischemic attack, disseminated intravascular coagulation syndrome, thrombotic microangiopathy, thrombosis phlebitis, deep vein thrombosis, idiopathic thrombosis, cerebral infarction (cerebral thrombosis, cerebral embolism), myocardial infarction, and pulmonary thromboembolism. In particular, a cytoprotective agent according to the present invention can be used favorably with respect to cerebral infarction.

A triprenyl phenol compound to be contained as an active ingredient in a cytoprotective agent according to the present invention is a triprenyl phenol compound represented by the general formula (I). A cytoprotective agent according to the present invention contains at least 1 triprenyl phenol compound according to the present invention as an active ingredient.

In the general formula (I), X is —CHY—$C(CH_3)_2Z$, and Y and Z are each independently —H or —OH, or jointly form a single bond. R represents a hydrogen atom or a substituent with a molecular weight of 1000 or less.

As the substituent with a molecular weight of 1000 or less, preferable is a substituent with the molecular weight of 800 or less, more preferable is a substituent with the molecular weight of 700 or less, and further preferable is a substituent with the molecular weight of 600 or less, from a viewpoint of the efficacy as a cytoprotective agent.

As the triprenyl phenol compound according to the present invention, that obtained by a chemical synthesis as well as that obtained by purifying a culture of a filamentous bacterium, for example Stachybotrys microspora, can be utilized. Examples of a method for obtaining a triprenyl phenol compound according to the present invention by purifying a culture of a filamentous bacterium includes a method comprising purification of an object compound from a culture to be obtained by adding a pre-determined additive organic amino compound to a culture liquid of Stachybotrys microspora. Such a method is described, for example, in Japanese Patent Laid-Open No. 2004-224737, Japanese Patent Laid-Open No. 2004-224738, and WO 2007/111203.

With respect to a triprenyl phenol compound according to the present invention, an enantiomer, a diastereomer, and a mixture of enantiomers or a mixture of diastereomers can be utilized. Such an enantiomer, a diastereomer, and a mixture of enantiomers or a mixture of diastereomers may be obtained by a chemical synthesis or by purification of a culture of a filamentous bacterium. In case it is obtained by purification of a culture of a filamentous bacterium, by using a D-isomer or an L-isomer of an additive organic amino compound to be added to a culture medium of a filamentous bacterium, the corresponding isomer can be obtained.

In case the R of a triprenyl phenol compound according to the present invention is a substituent with a molecular weight of 1000 or less, specific examples include a triprenyl phenol compound represented by the following general formula (II) or (III).

[Triprenyl Phenol Compound Represented by General Formula (II)]

One of the specific examples of a triprenyl phenol compound according to the present invention is a compound represented by the following general formula (II).

(II)

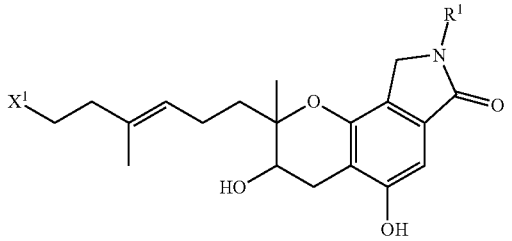

In the general formula (II), $X^1$ is —CHY—$C(CH_3)_2Z$, and Y and Z are each independently —H or —OH, or jointly form a single bond.

$R^1$ represents any one among the following (A) through (D):

(A) a residue of an amino compound selected from the group consisting of a natural amino acid, a D-isomer of a natural amino acid, and a compound derived by substituting a carboxy group in a natural amino acid or a D-isomer of a natural amino acid by a hydrogen atom, a hydroxy group, or a hydroxymethyl group, from which one amino group has been removed (provided that —$(CH)_2$—OH is excluded);

(B) an aromatic group having at least one selected from the group consisting of a carboxy group, a hydroxy group, a sulfonic group and a secondary amino group as a substituent or a part of a substituent, or an aromatic group that contains a secondary amino group and may contain a nitrogen atom;

(C) an aromatic amino acid residue represented by the following formula (II-1):

(II-1)

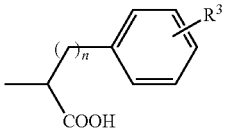

wherein $R^3$ is a substituent, which may be present or absent, representing at least one substituent selected from the group consisting of a hydroxy group, a carboxy group, and a C1 to C5 alkyl group, and n represents an integer of 0 or 1; or (D) a substituent represented by $-L^1-L^2-R^4$, wherein $L^1$ represents a linking group comprising a C1 to C4 alkylene group having a carboxy group, $L^2$ represents a linking group expressed by —NH—C(═O)— or —NH—C(═S)—NH—, and $R^4$ represents a 9-fluorenylalkyloxy group having a C1 to C3 alkyloxy group, or a polyheterocyclic group represented by the following formula (II-2):

(II-2)

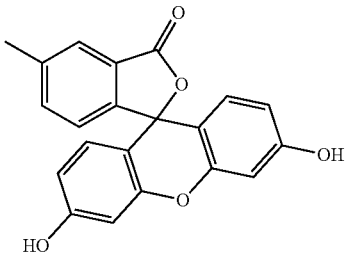

A compound according to the general formula (II), in which $R^1$ is the (A), will be described.

The (A) is a residue of an amino compound selected from the group consisting of a natural amino acid, a D-isomer of a natural amino acid, and a compound derived by substituting a carboxy group in a natural amino acid or a D-isomer of a natural amino acid by a hydrogen atom, a hydroxy group, or a hydroxymethyl group, from which one amino group has been removed (provided that —$(CH)_2$—OH is excluded).

There is no particular restriction on a natural amino acid insofar as it is an amino acid able to exist naturally, and examples thereof include an α-amino acid, a β-amino acid, a γ-amino acid and a δ-amino acid. Such an amino acid may be obtained from a natural product, or artificially by means of an organic synthesis or otherwise.

Examples of a natural amino acid include, as an α-amino acid, glycine, alanine, threonine, valine, isoleucine, tyrosine, cysteine, cystine, methionine, histidine, aspartic acid, glutamic acid, asparagine, glutamine, arginine, lysine, hydroxylysine, ornithine, citrulline, homocysteine, 3,4-dihydroxyphenylalanine, homocystine, diaminopimelic acid, diaminopropionic acid, serine, leucine, phenylalanine and tryptophan; as a β-amino acid, β-alanine; as a γ-amino acid, γ-aminobutyric acid and carnitine; and as a δ-amino acid, 5-aminolevulinic acid and 5-aminovaleric acid.

Examples of a compound derived by substituting a carboxy group in the natural amino acid and a D-isomer of the natural amino acid by a hydrogen atom, a hydroxy group, or a hydroxymethyl group include an amino alcohol and an amine. Examples of the amino alcohol include 2-aminoethanol.

Specific examples of a compound according to the general formula (II), in which $R^1$ is the (A), include the compounds shown in the following Table 1. "Additive Organic Amino Compound" in the Table means such an additive organic amino compound as is used, when a triprenyl phenol compound is obtained by purification of a culture obtained by adding a pre-determined additive organic amino compound to a culture liquid of Stachybotrys microspora (hereinafter the same shall apply).

TABLE 1

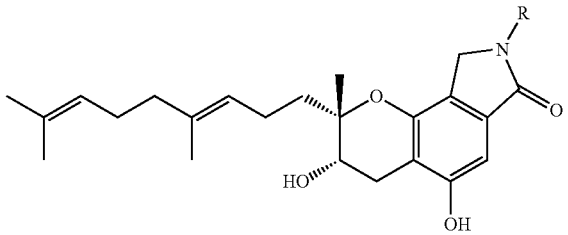

SMTPs

| Compound No | Molecular Mass | R = | Additive Organic Amino Compound |
|---|---|---|---|
| SMTP-3 | 473.6 | 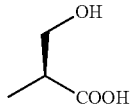 | L-serine |
| SMTP-4 | 533.7 | 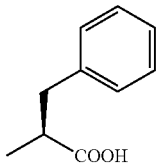 | L-phenylalanine |
| SMTP-4Me | 547.7 | 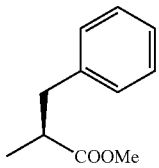 | L-phenylalanine methylester |

TABLE 1-continued

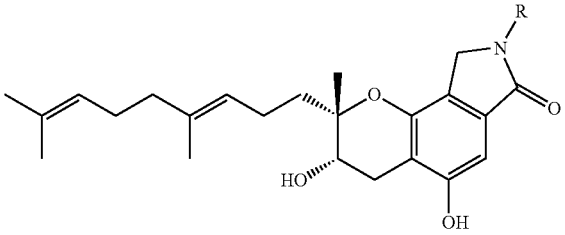

SMTPs

| Compound No | Molecular Mass | R = | Additive Organic Amino Compound |
|---|---|---|---|
| SMTP-4D | 533.7 | 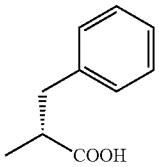 | D-phenylalanine |
| SMTP-5 | 499.6 | 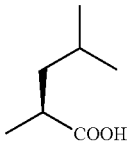 | L-leucine |
| SMTP-5D | 499.6 | 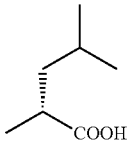 | D-leucine |
| SMTP-6 | 572.7 | 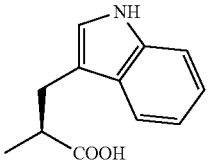 | L-tryptophan |
| SMTP-6D | 572.7 | 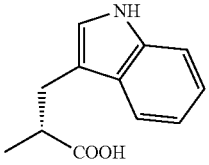 | D-tryptophan |
| SMTP-10 | 499.6 | 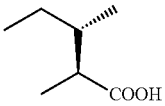 | L-isoleucine |
| SMTP-11 | 485.6 | 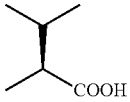 | L-valine |
| SMTP-12 | 457.6 | 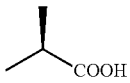 | L-glycine |
| SMTP-13 | 517.7 | 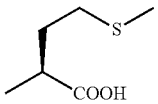 | L-methionine |

TABLE 1-continued

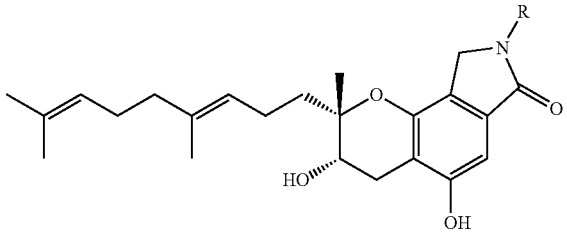

SMTPs

| Compound No | Molecular Mass | R = | Additive Organic Amino Compound |
|---|---|---|---|
| SMTP-14 | 549.7 | 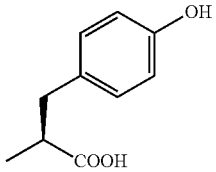 | L-tyrosine |
| SMTP-15 | 542.7 | 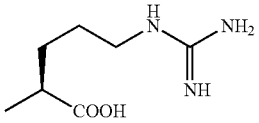 | L-arginine |

A compound shown in the above Table 1 can be used favorably as a triprenyl phenol compound according to the present invention.

A compound according to the general formula (II), in which $R^1$ is the (B), will be described.

The (B) is an aromatic group having at least one selected from the group consisting of a carboxy group, a hydroxy group, a sulfonic group and a secondary amino group as a substituent or a part of a substituent, or an aromatic group that contains a secondary amino group and may contain a nitrogen atom.

Examples of the aromatic group include a compound expressed by the following structural formulas.

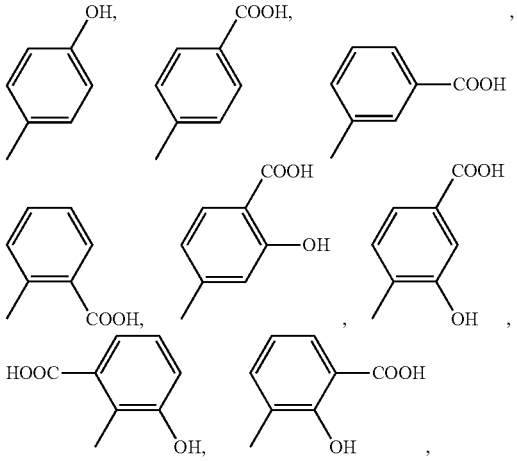

-continued

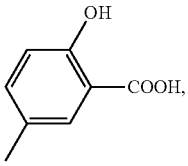

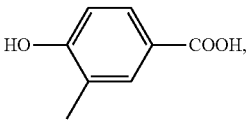

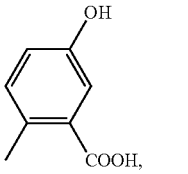

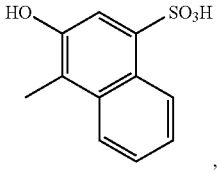

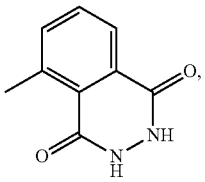

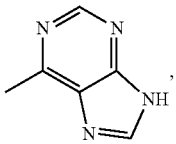

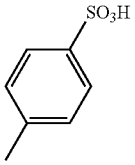

Specific examples of a compound according to the general formula (II), in which $R^1$ is the (B), include the compounds shown in the following Table 2.

TABLE 2

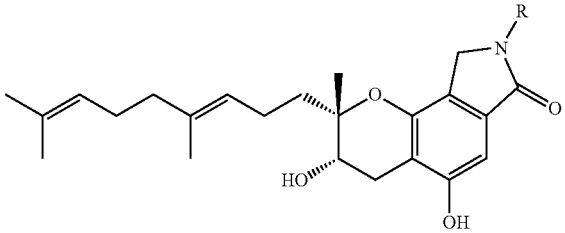

SMTPs

| Compound No | Molecular Mass | R = | Additive Organic Amino Compound |
|---|---|---|---|
| SMTP-18 | 477.6 | 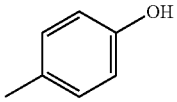 | p-aminophenol |
| SMTP-19 | 505.6 | 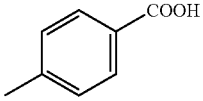 | p-aminobenzoic acid |
| SMTP-20 | 505.6 | 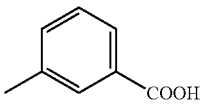 | m-aminobenzoic acid |

TABLE 2-continued

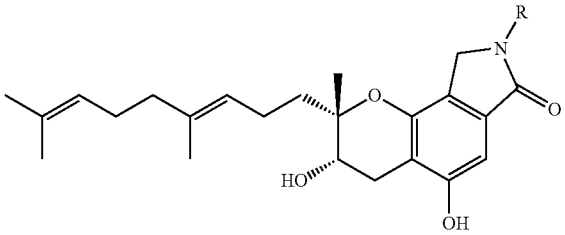

SMTPs

| Compound No | Molecular Mass | R = | Additive Organic Amino Compound |
|---|---|---|---|
| SMTP-21 | 505.6 | 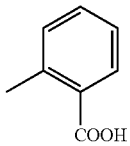 | o-aminobenzoic acid |
| SMTP-22 | 521.6 | 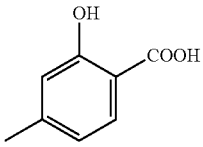 | 4-aminosalicyclic acid |
| SMTP-23 | 521.6 | 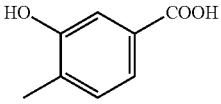 | 4-amino-3-hydroxybenzoic acid |
| SMTP-24 | 521.6 | 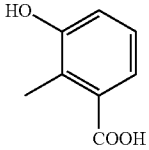 | 3-hydroxy-anthranilic acid |
| SMTP-25 | 521.6 | 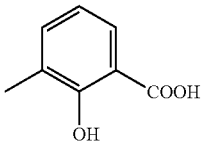 | 3-aminosalicyclic acid |
| SMTP-26 | 521.6 | 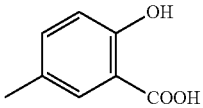 | 5-aminosalicyclic acid |
| SMTP-27 | 521.6 | 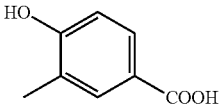 | 3-amino-4-hydroxybenzoic acid |
| SMTP-28 | 521.6 | 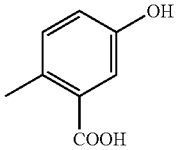 | 5-hydroxy-anthranilic acid |

TABLE 2-continued

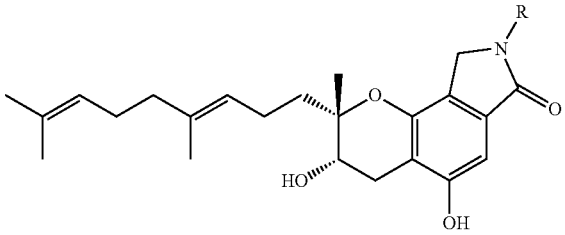

SMTPs

| Compound No | Molecular Mass | R = | Additive Organic Amino Compound |
|---|---|---|---|
| SMTP-32 | 503.6 | 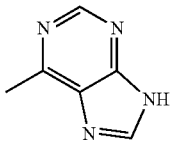 | adenine or adenosine |
| SMTP-36 | 545.3 | 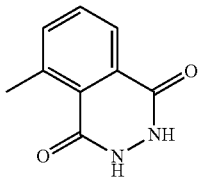 | 5-amino-2,3-dihydro-1,4-phthalazinedione |
| SMTP-37 | 607.7 | 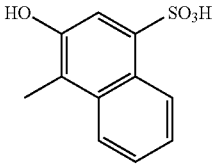 | 1-amino-2-naphthol-4-sulfonic acid |
| SMTP-42 | 541.7 | 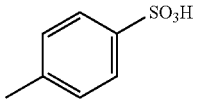 | p-sulfanilic acid |

A compound shown in the above Table 2 can be used favorably as a triprenyl phenol compound according to the present invention.

A compound according to the general formula (II), in which $R^1$ is the (C), will be described.

The (C) is an aromatic amino acid residue represented by the following formula (II-1); wherein $R^3$ is a substituent, which may be present or absent, representing at least one substituent selected from the group consisting of a hydroxy group, a carboxy group, and a C1 to C5 alkyl group, and n represents an integer of 0 or 1.

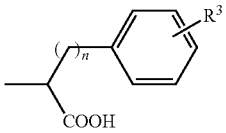

(II-1)

Examples of an aromatic amino acid residue represented by the formula (II-1) include the compounds represented by the following structural formulas.

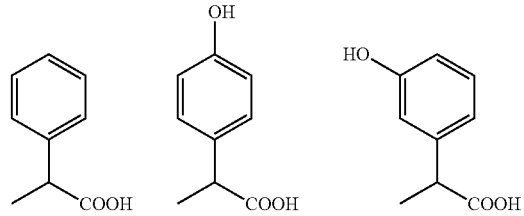

Specific examples of a compound according to the general formula (II), in which $R^1$ is the (C), include the compounds shown in the following Table 3.

TABLE 3

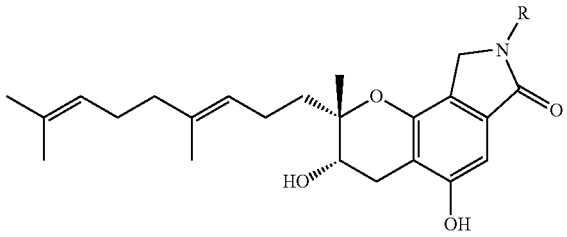

SMTPs

| Compound No | Molecular Mass | R = | Additive Organic Amino Compound |
|---|---|---|---|
| SMTP-43 | 519.6 | 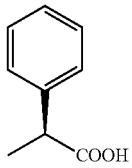 | L-phenylglycine |
| SMTP-43D | 519.6 | 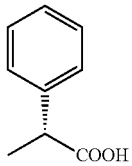 | D-phenylglycine |
| SMTP-44 | 535.6 | 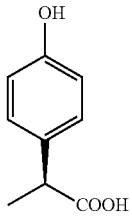 | L-4-hydroxy-phenyl-glycine |
| SMTP-44D | 535.6 | 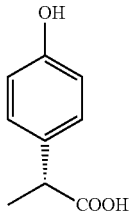 | D-4-hydroxy-phenyl-glycine |

TABLE 3-continued

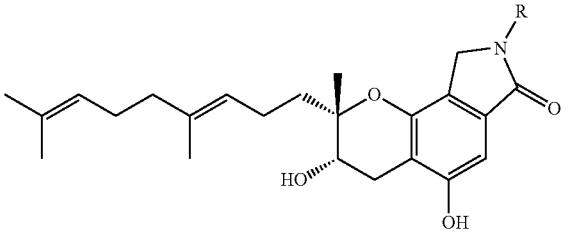

SMTPs

| Compound No | Molecular Mass | R = | Additive Organic Amino Compound |
|---|---|---|---|
| SMTP-45-I | 535.6 | 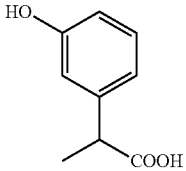 | DL-3-hydroxyphenyl-glycine |
| SMTP-45-II | 535.6 | 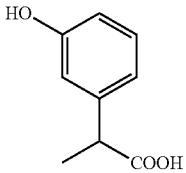 | DL-3-hydroxyphenyl-glycine |

A compound shown in the above Table 3 can be used favorably as a triprenyl phenol compound according to the present invention.

A compound according to the general formula (II), in which $R^1$ is the (D), will be described.

The (D) is a substituent represented by $-L^1-L^2-R^4$, wherein $L^1$ represents a linking group comprising a C1 to C4 alkylene group having a carboxy group, $L^2$ represents a linking group expressed by —NH—C(═O)— or —NH—C(═S)—NH—, and $R^4$ represents a 9-fluorenylalkyloxy group having a C1 to C3 alkyloxy group, or a polyheterocyclic group represented by the following formula (II-2).

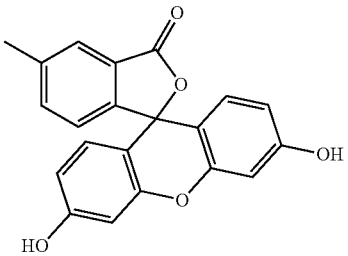

(II-2)

Specific examples of a compound according to the general formula (II), in which $R^1$ is the (D), include the compounds shown in the following Table 4.

TABLE 4

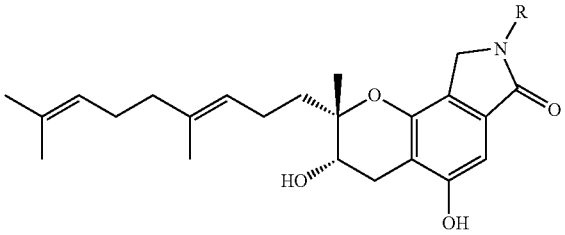

SMTPs

| Compound No | Molecular Mass | R = | Additive Organic Amino Compound |
|---|---|---|---|
| SMTP-46 | 722.9 | 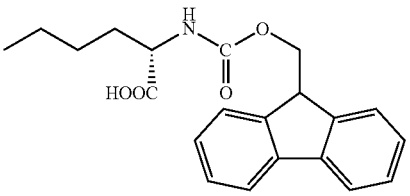 | Nα-Fmoc-L-omithine |
| SMTP-47 | 722.9 | 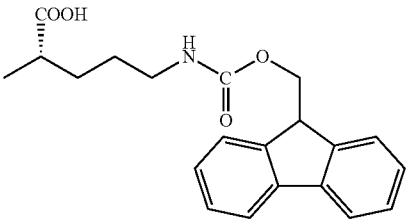 | Nδ-Fmoc-L-omithine |

TABLE 4-continued

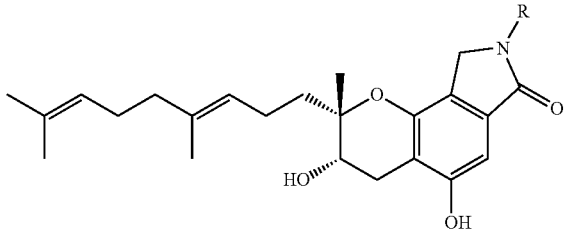

SMTPs

| Compound No | Molecular Mass | R = | Additive Organic Amino Compound |
|---|---|---|---|
| SMTP-48 | 890.0 | 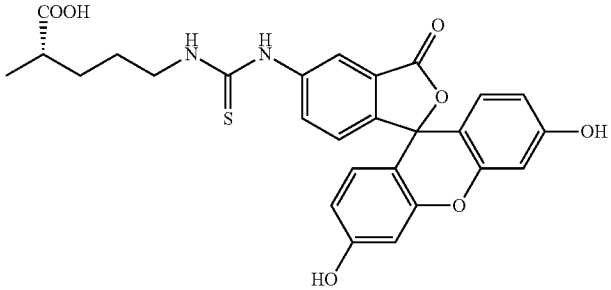 | Nδ-FITC-L-omithine |
| SMTP-49 | 890.0 | 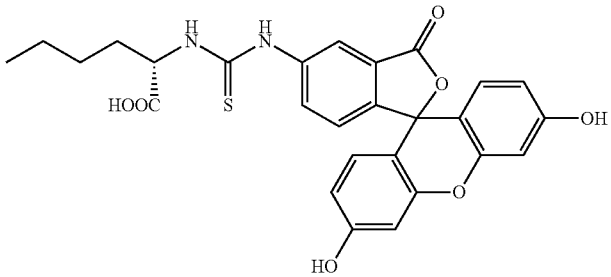 | Nα-FITC-L-omithine |

A compound shown in the above Table 4 can be used favorably as a triprenyl phenol compound according to the present invention.

[Triprenyl Phenol Compound Represented by the General Formula (III)]

One of the specific examples of a triprenyl phenol compound according to the present invention is a compound represented by by the following general formula (III).

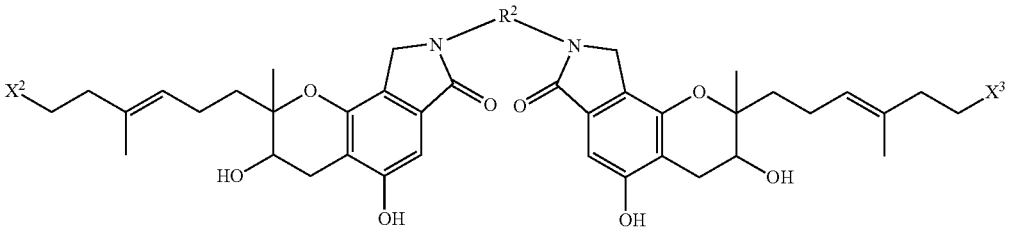

(III)

In the general formula (III), $X^2$ and $X^3$ are each independently —CHY—$C(CH_3)_2Z$; Y and Z are each independently —H or —OH, or jointly form a single bond. $R^2$ represents a residue of an amino compound selected from the group consisting of a natural amino acid with two amino groups, a D-isomer of a natural amino acid with two amino groups, a compound derived by substituting a carboxy group in a natural amino acid with two amino groups or a D-isomer of a natural amino acid with two amino groups by a hydrogen atom, a hydroxy group, or a hydroxymethyl group, compounds represented by $H_2N$—CH(COOH)—$(CH_2)_n$—$NH_2$ (n being an integer from 0 to 9), and compounds represented by $H_2N$—CH(COOH)—$(CH_2)_m$—$S_p$—$(CH_2)_q$—CH(COOH)—$NH_2$ (m, p and q each independently being an integer from 0 to 9), from which two amino groups have been removed.

The n represents an integer from 0 to 9, preferably an integer from 0 to 6, more preferably an integer from 1 to 5, and further preferably an integer from 1 to 4.

The m represents an integer from 0 to 9, preferably an integer from 0 to 4, more preferably an integer from 1 to 3, and further preferably 1 or 2.

The p represents an integer from 0 to 9, preferably an integer from 0 to 4, more preferably an integer from 1 to 3, and further preferably 1 or 2.

The q represents an integer from 0 to 9, preferably an integer from 0 to 4, more preferably an integer from 1 to 3, and further preferably 1 or 2.

If the p is 0, m+q is preferably an integer from 0 to 9, more preferably an integer from 0 to 6, further preferably an integer from 1 to 5, and especially preferably an integer from 1 to 4.

Examples of a natural amino acid with 2 amino groups include, as an α-amino acid, hydroxylysine, citrulline, cystine, homocystine, diaminopimelic acid, diaminopropionic acid, lysine and ornithine.

Examples of a compound derived by substituting a carboxy group in a natural amino acid with 2 amino groups and a D-isomer of a natural amino acid with 2 amino groups by a hydrogen atom, a hydroxy group, or a hydroxymethyl group include $H_2N—(CH_2)_k—NH_2$ (k is an integer from 1 to 10, preferably an integer from 1 to 6, and more preferably an integer from 1 to 4).

Specific examples of a compound represented by the general formula (III) include the compounds shown in the following Table 5.

TABLE 5

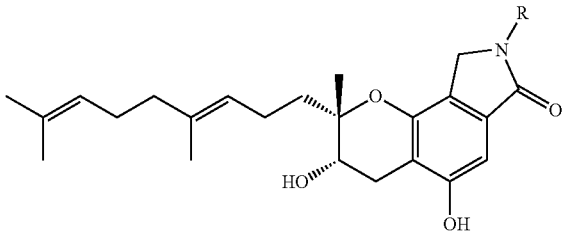

SMTPs

| Compound No | Molecular Mass | R = | Additive Organic Amino Compound |
|---|---|---|---|
| SMTP-7 | 869.1 | 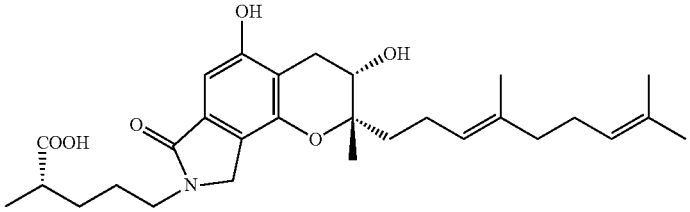 | L-omithine |
| SMTP-7D | 869.1 | 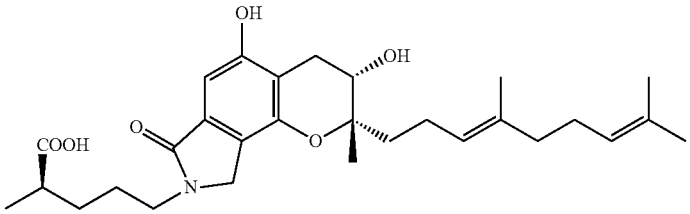 | D-omithine |
| SMTP-8 | 883.1 | 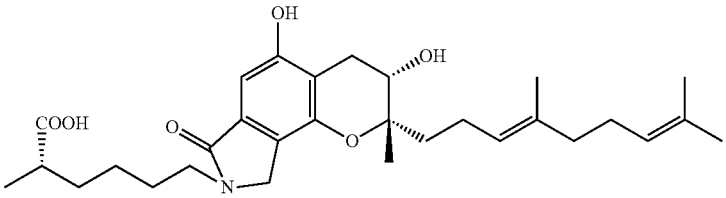 | L-lysine |
| SMTP-8D | 883.1 | 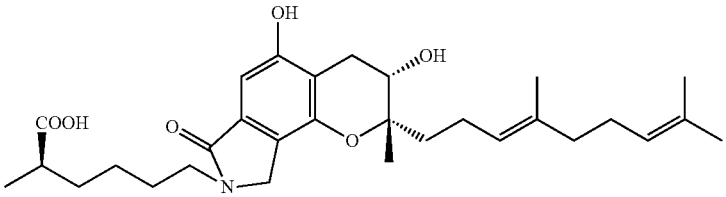 | D-lysine |

TABLE 5-continued

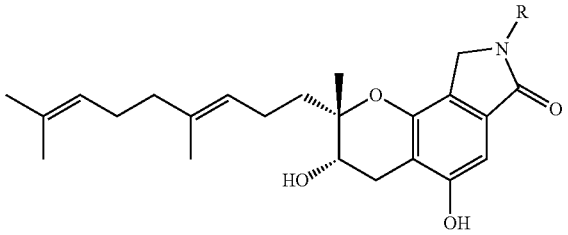

SMTPs

| Compound No | Molecular Mass | R = | Additive Organic Amino Compound |
|---|---|---|---|
| SMTP-9 | 977.2 | 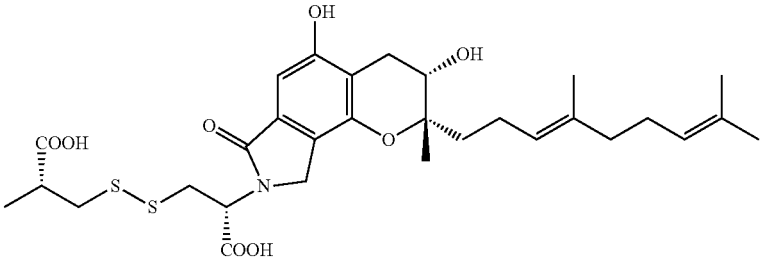 | L-cystine |
| SMTP-29 | 839.1 | 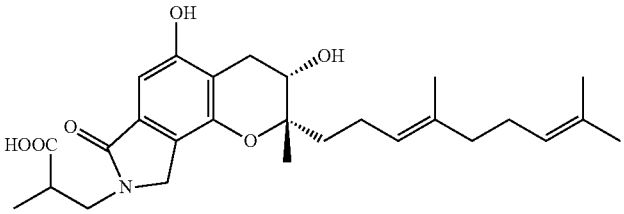 | DL-2,3-diaminopropionic acid |
| SMTP-31 | 925.2 | 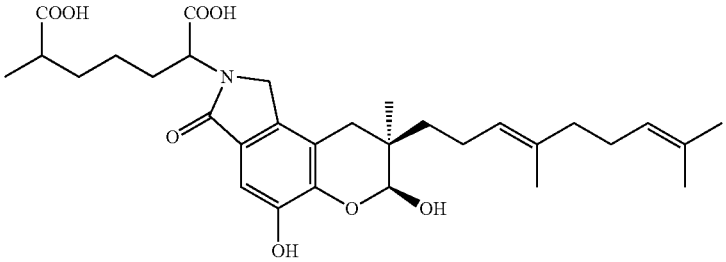 | DL-2,6-diaminopinelic acid |

A compound shown in the above Table 5 can be used favorably as a triprenyl phenol compound according to the present invention.

Specific examples of a compound represented by the general formula (I) include, in addition to a triprenyl phenol compound represented by the general formula (II) or (III), the triprenyl phenol compounds shown in the following Table 6.

TABLE 6

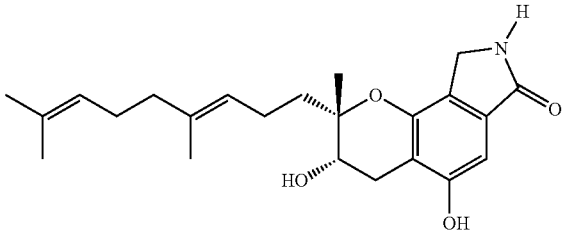

SMTP-0

TABLE 6-continued

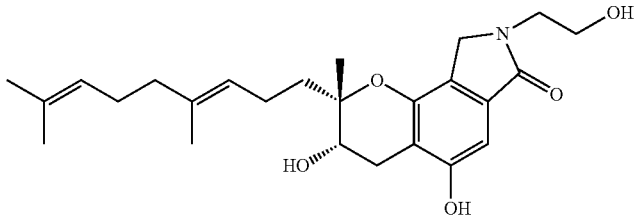

SMTP-1

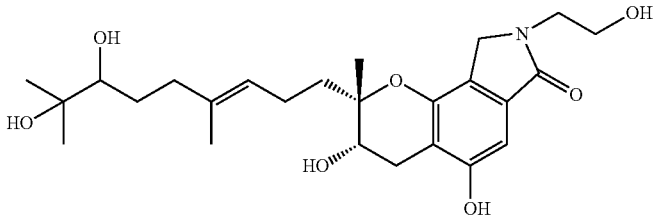

SMTP-2

| Compound No | Molecular Mass | Additive Organic Amino Compound |
|---|---|---|
| SMTP-0 | 385.5 | ammonium chloride |
| SMTP-1 | 429.6 | 2-aminoethanol |
| SMTP-2 | 463.3 | 2-aminoethanol |

A compound shown in the above Table 6 can be used favorably as a triprenyl phenol compound according to the present invention.

A triprenyl phenol compound according to the present invention can be used in a liberated form, in a form of a pharmaceutically permissible salt or an ester, or in a form of a solvate. An inorganic acid, such as hydrochloric acid, hydrobromic acid, sulfuric acid, nitric acid, phosphoric acid, and an organic acid, such as citric acid, formic acid, fumaric acid, malic acid, acetic acid, succinic acid, tartaric acid, methanesulfonic acid, and p-toluenesulfonic acid are favorably used for forming a pharmaceutically permissible salt of a compound according to the present invention. Further, a compound containing an alkali metal, such as sodium, potassium, calcium, and magnesium, or an alkaline-earth metal, a basic amine, and a basic amino acid are also advantageous for forming a pharmaceutically permissible salt of a compound according to the present invention. Further, a C1 to C10 alcohol or a carboxylic acid, preferably methyl alcohol, ethyl alcohol, acetic acid, or propionic acid, is advantageous for forming a pharmaceutically permissible ester of a compound according to the present invention. Further, water is also advantageous for forming a pharmaceutically permissible solvate of a compound according to the present invention.

There is no particular restriction on a kind of a carrier or a formulation additive to be used for preparing a cytoprotective agent according to the present invention. A cytoprotective agent according to the present invention is formulated using a triprenyl phenol compound according to the present invention, and a pharmaceutically permissible solid carrier (e.g. gelatin, and lactose) or liquid carrier (e.g. water, a physiological saline solution, and a glucose aqueous solution).

Depending on a kind of a triprenyl phenol compound to be used as an active ingredient, the seriousness of ischemic damage and a location of an affected part in the body, a cytoprotective agent according to the present invention is administered preferably at 0.01 to 100 mg/kg as a single effective dose for an adult, and more preferably administered at 0.1 to 30 mg/kg. There is no particular restriction on the number of administrations, and the use by any of one-time administration, multiple administrations, and a continuous administration is acceptable. The administration interval and administration duration can be selected by those skilled in the art according to clinical findings, image diagnostic findings, hematological findings, a comorbid disease, past history, etc.

If a cytoprotective agent according to the present invention is used by multiple administrations, from a viewpoint of a sustainable contact of an affected part with the cytoprotective agent according to the present invention, a mode with administrations immediately after the onset of a symptom and 12 hours after the onset is preferable, and a mode with a continuous administration for 1 hour to 24 hours per day is also preferable.

There is no particular restriction on an administration means to an adult, and various administration routes, such as intravenous administration, subcutaneous administration, intramuscular administration, and oral administration, can be selected. For example, at an acute phase of various diseases, an intravenous administration, more precisely an intravenous injection or a drip infusion is preferable from a viewpoint of rapid and sure administration of a desired dose to a patient. For example, those skilled in the art may choose a rapid intravenous injection for 10% of a single dose, and a drip infusion over 30 min to 1 hour for 90% thereof.

A cytoprotective agent according to the present invention can be used without any particular restriction in a period, in which the possibility of cell damage caused by ischemia increases. Examples of "a period in which the possibility of cell damage increases" include a period affected by the above-described various thromboses. Further a period during or after a treatment of thrombosis utilizing an anticoagulant, an antiplatelet, a thrombolytic drug, etc. may be included. A period after the recovery from thrombosis may be also included, and in the period the cytoprotective agent may be used prophylactically.

If it is possible that cell damage should be caused by ischemia, the same may be used without limitation to the above-described periods.

A cytoprotective agent according to the present invention may be used singly or together with one or more thrombolytic drugs.

By combined use of a cytoprotective agent according to the present invention and a thrombolytic drug, the therapeutic effect is expected to be enhanced by inhibiting effectively dysfunction by ischemia reperfusion damage caused by thrombolysis due to a thrombolytic drug. In this case, a cytoprotective agent according to the present invention and a thrombolytic drug may be used at the same time or separately at different times.

Examples of a thrombolytic drug usable in combination include alteplase, urokinase, desmoteplase, and monteplase.

A cytoprotective agent according to the present invention is effectual to a group of patients, to whom a thrombolytic drug is not any more applicable, because long time has passed after the onset of a symptom. In case of cerebral infarction, it is effectual to use a cytoprotective agent according to the present invention for a patient to whom, for example, alteplase cannot be administered, because 3 or more hours have passed after the onset of a symptom. In this connection, if the onset time is not clear, the latest symptomless time (the latest time when a patient was confirmed as symptomless) is deemed as the onset time.

If a cytoprotective agent according to the present invention is used against thrombosis (including thromboembolism), it is effectual to use it for a patient to whom a thrombolytic drug is contraindicated. It is also effectual to use a cytoprotective agent according to the present invention for a patient, who has discontinued administration of a thrombolytic drug due to appearance of a sign or a symptom of contraindication during the administration of a thrombolytic drug. Such contraindications include hemorrhagic diathesis, hemorrhage, hypertension, and impaired blood glucose. For example, in case of cerebral infarction, for a patient to whom a thrombolytic drug cannot be administered, because the risk of intracranial hemorrhage would be increased, a cytoprotective agent according to the present invention may be used.

If a cytoprotective agent according to the present invention is used against thrombosis (including thromboembolism), it is effectual to use it for those among patients of thrombosis, to whom a thrombolytic drug is usually unable to use for treatment. Examples of such patients include patients of transient ischemic attack, disseminated intravascular coagulation syndrome, thrombotic microangiopathy, thrombosis phlebitis, deep vein thrombosis, and idiopathic thrombosis.

A cytoprotective agent according to the present invention can be used without limitation to the use for humans. Examples of another subject for application include a domestic animal, such as a cattle, a horse, and a sheep, and a pet, such as a dog, a cat and a monkey.

The present invention includes a method of treatment of ischemic damage including administration of a drug containing a triprenyl phenol compound according to the present invention to a patient affected by ischemic damage. With respect to the method of treatment of ischemic damage according to the present invention, the term "treatment" means improvement of a symptom, which includes inhibition of aggravation, and reduction or relaxation, of a symptom.

By the method of treatment of ischemic damage according to the present invention, inhibition of aggravation of ischemic damage, or reduction or relaxation of a symptom, can be attained.

The dose, administration interval, administration duration, and administration method of a drug containing a triprenyl phenol compound according to the present invention for a method of treatment of ischemic damage according to the present invention are similar to the cytoprotective agent according to the present invention described above.

The method of treatment of ischemic damage according to the present invention is favorably applicable to thrombosis (including also thromboembolism) as ischemic damage, and more favorably applicable to cerebral infarction.

One mode of the method of treatment of ischemic damage according to the present invention is a method of treatment of ischemic damage including administration of a drug containing a triprenyl phenol compound according to the present invention to a patient during a period in which the possibility of cell damage caused by ischemia increases. The expression "a period in which the possibility of cell damage increases" is as described above. The use of this method of treatment is favorably applied to thrombosis (including also thromboembolism), which is a type of ischemic damage, and its use with respect to cerebral infarction is more favorable.

One mode of the method of treatment of ischemic damage according to the present invention is a method of treatment of ischemic damage including use of a drug containing a triprenyl phenol compound according to the present invention together with one or more thrombolytic drugs. The use of this method of treatment is favorably applied to thrombosis (including also thromboembolism), which is a type of ischemic damage, and its use with respect to cerebral infarction is more favorable.

Examples of a thrombolytic drug to be used together with a drug containing a triprenyl phenol compound according to the present invention include alteplase, urokinase, desmoteplase, and monteplase. A drug containing a triprenyl phenol compound according to the present invention and a thrombolytic drug may be administered to a patient at the same time or separately at different times.

One mode of the method of treatment of ischemic damage according to the present invention is a method of treatment of ischemic damage including administration of a drug containing a triprenyl phenol compound according to the present invention to a patient 3 or more hours after the onset of a symptom. The use of this method of treatment is favorably applied to thrombosis (including also thromboembolism), which is a type of ischemic damage, and its use with respect to cerebral infarction is more favorable.

For example, in the case of cerebral infarction, it is effectual to use a drug containing a triprenyl phenol compound according to the present invention for a patient to whom alteplase cannot be administered because 3 or more hours have passed since the onset of a symptom. In this regard, if the onset time is not clear, the latest symptomless time (the latest time when a patient was confirmed as being symptomless) is deemed as the onset time.

One mode of the method of treatment of ischemic damage according to the present invention is a method of treatment of ischemic damage including administration of a drug containing a triprenyl phenol compound according to the present invention to a patient to whom a thrombolytic drug is contraindicated. The use of this method of treatment is favorably applied to thrombosis (including also thromboembolism), which is a type of ischemic damage, and its use with respect to cerebral infarction is more favorable.

Such contraindications include hemorrhagic diathesis, hemorrhage, hypertension, and impaired blood glucose. For example, in the case of cerebral infarction, for a patient to whom a thrombolytic drug cannot be administered because the risk of intracranial hemorrhage would be increased, a drug containing a triprenyl phenol compound according to the present invention may be administered.

One mode of the method of treatment of ischemic damage according to the present invention is a method of treatment of ischemic damage including administration of a drug containing a triprenyl phenol compound according to the present invention to a patient to whom a thrombolytic drug is not usually usable for treatment. The use of this method of treatment is favorably applied to thrombosis (including also thromboembolism), which is a type of ischemic damage, and its use with respect to cerebral infarction is more favorable.

Examples of a patient to whom a thrombolytic drug is not usually usable for treatment, include patients of transient ischemic attack, disseminated intravascular coagulation syndrome, thrombotic microangiopathy, thrombosis phlebitis, deep vein thrombosis, and idiopathic thrombosis.

One mode of the method of treatment of ischemic damage according to the present invention is a method of treatment of ischemic damage including administration of a drug containing a triprenyl phenol compound according to the present invention to a patient who is suffering from or predicted to suffer from ischemia reperfusion damage. The use of this method of treatment is favorably applied to thrombosis (including also thromboembolism), which is a type of ischemic damage, and its use with respect to cerebral infarction is more favorable.

By the above method of treatment of ischemic damage, prevention of ischemia reperfusion damage, inhibition of aggravation, or reduction or relaxation of a symptom can be attained.

EXAMPLES

The present invention will now be described by way of examples thereof, provided that the invention should not be limited thereto. Unless otherwise specified herein, "%" is by mass.

Example 1

Production of Cerebral Infarction Model Using Acetic Acid

[Mongolian Gerbil Cerebral Infarction Model]

Anesthesia was induced to a male Mongolian gerbil (body weight 55 to 65 g) by inhalation of 5% isoflurane (trade name Escain, Mylan Inc.), and maintained with 1 to 1.5% isoflurane. The Mongolian gerbil was fixed in a dorsal position, and the neck was dehaired and then disinfected with 70% ethanol. After median incision of the neck, the right common carotid artery was detached, clamped to block the blood flow temporarily, and coated with 100% acetic acid by 30 reciprocating motions so as to produce a thrombus. The blood vessel was reopened after 10 min of the blockage of the blood flow to transfer the thrombus by the blood stream into the brain to make it ischemic and generate cerebral infarction. The operating field was closed with an instant adhesive (trade name Aron Alpha (Krazy Glue), Toagosei Co., Ltd.) and disinfected with 70% ethanol.

[Evaluation of Neurological Symptom]

Twenty four hours after the initiation of the operation neurological symptoms were observed as an indicator for cerebral infarction. Many types of neurological symptoms specific to cerebral infarction, such as extension of a hindlimb or circling to one direction, have been reported. Applying a modified evaluation method of the method proposed by Longa, et al. (Stroke 1989; 20:84-91) postoperative neurological symptoms were evaluated as per: no deficit, 0; extension of limb, 1; circling to one direction, 2; incline posture, 3; diminished motion, 4.

With respect to statistical analysis, for multiple comparisons was conducted firstly one-way analysis of variance (ANOVA) and then a Bonferroni test was conducted, if significant difference is detected. Significant difference was positively recognized with significance level 5% ($P<0.05$). All the results are expressed in mean±standard error.

[Evaluation of Infarction Area Percentage]

After the evaluation of neurological symptoms according to the above method, the animal was decapitated under anesthesia with isoflurane. The cranial bone was exfoliated of skin and opened, and, after scission of optic nerve, the brain was extirpated and dipped in a physiological saline solution to remove attached body hairs, etc. The extirpated brain was placed in a brain matrix (RBM-1000C, ASI Instruments) to carry out coronal slicing from the frontal pole at thickness of 2 mm. The slices were dipped in 2% 2,3,5-triphenyl-2H-tetrazolium chloride (TTC), and incubated for staining at 37° C. for 30 min in a $CO_2$ incubator. The colorless TTC is reduced by hydrogen liberated by the action of dehydrogenase contained in a normal cell converting to dark red colored water-insoluble 1,3,5-triphenylformazan (TPF), so that the normal cell is stained. Unstained area (white area) was defined as an infarction area. Meanwhile, the corpus callosum, which is commissural fibers connecting the right and left cerebral hemispheres, is not stained and is white, and therefore image processing for the analyses as described below was conducted excluding the corpus callosum.

After staining images of the brain slices were taken by a digital camera under a stereoscopic microscope. For analysis of the infarction area percentage, an image analysis software Image J (Version 1.4) was used. Full, excluding the corpus callosum, images of the taken 2nd, 3rd, and 4th brain slice images were converted to grayscale. From the grayscale images a histogram for the whole brain as the object scope was obtained showing in the ordinate the frequency of occurrence (frequency) at certain brightness, and showing in the abscissa the brightness (0 to 255). The sum from 0 to 255 was defined as the area size of the whole brain, and the sum from 160 to 219 was defined as the area size of the infarction area. Then the infarction area percentage was determined according to the following formula using the total area size of the infarction areas and the total area size of the whole brain, of the 3 brain slice images. Statistical analysis was conducted as above.

Infarction area percentage (%)=Total area size of infarction areas excluding corpus callosum/Total area size of the whole brain×100

[Mouse Cerebral Infarction Model]

Using male ddY line mouse (body weight 35 to 45 g), a cerebral infarction model was produced and evaluated about neurological symptoms and the infarction area percentage according to methods similar to the production method and the evaluation method for the Mongolian gerbil cerebral infarction model.

Example 2

Comparison of Effectiveness of Various Drugs on Mongolian Gerbil Cerebral Infarction Model The improvement effectiveness of SMTP-7, alteplase and edaravone (cerebroprotective drug) on the infarction area percentage and the neurological symptom was compared using the Mongolian gerbil cerebral infarction model. At the same time the dose dependence of the degree of improvement was investigated.

SMTP-7 was produced according to a process described in Japanese Patent Laid-Open No. 2004-224738 by purifying a culture obtained by adding L-ornithine as an additive organic amino compound to a culture medium of Stachybotrys microspora, strain IFO30018. To SMTP-7 produced through purification and exsiccated, 0.3 N NaOH and a physiological saline solution (0.9% NaCl) were added to prepare a 50 mg/mL solution. Thereafter, the solution was adjusted to 10 mg/mL, and weak alkaline pH with 0.3 N HCl and a physiological saline solution, subjected to filtration sterilization, divided into small fractions, and cryopreserved at −30° C. The SMTP-7 was used after dilution according to need with a physiological saline solution.

The SMTP-7 cryopreserved as above was dissolved at 1 mg/mL in a physiological saline solution just before a test. Alteplase (trade name Activacin, Kyowa Hakko Kirin Co., Ltd.) was dissolved in a solvent for Activacin at 1.03 mg/mL. As for Edaravone (trade name Radicut, Mitsubishi Tanabe Pharma Corp.), a stock solution of 1.5 mg/kg was used. The above medicaments were used after dilution according to need with a physiological saline solution.

The doses of SMTP-7 were set at 0.1 mg/kg, 1 mg/kg and 10 mg/kg; the doses of alteplase at 0.01 mg/kg, 0.1 mg/kg and 10 mg/kg; and the doses of edaravone at 1 mg/kg, 3 mg/kg and 10 mg/kg.

Administrations of SMTP-7 and alteplase were started 1 hour, 3 hours, or 6 hours after the initiation of ischemia of a Mongolian gerbil cerebral infarction model. An administration of edaravone was started immediately after (0 hour), 1 hour after, or 3 hours after the initiation of ischemia.

Anesthesia was induced to a Mongolian gerbil cerebral infarction model by inhalation of 5% isoflurane and thereafter maintained at 1 to 1.5%, so that an administration should be able to start as soon as the above defined time elapsed from the initiation of ischemia. The Mongolian gerbil was fixed in a dorsal position, and a polyethylene catheter with a 27 G needle was inserted into the left femoral vein. SMTP-7 and alteplase were administered through the catheter, wherein 10% of the dose by a bolus administration and the rest by a continuous administration over 30 min. Edaravone was administered continuously over 30 min. Six Mongolian gerbils were used for each condition.

Figure 2:
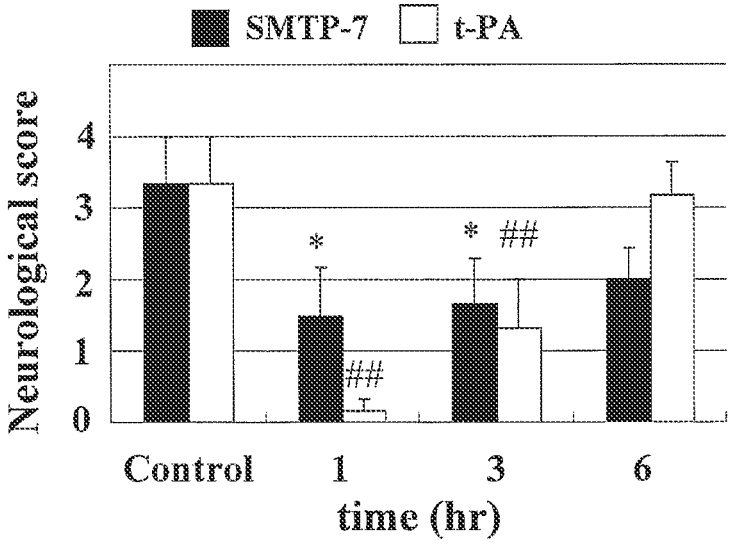
FIG. 2 is a diagram showing the neurological symptom in Example 2 according to the present invention.

Twenty four hours after the initiation of the operation neurological symptoms of the respective Mongolian gerbils were examined to rate the neurological symptom. Then the brain of each Mongolian gerbil was extirpated and the infarction area was measured and the infarction area percentage was determined. The infarction area percentage and scores of the neurological symptom are shown in Table 7. Further, for SMTP-7 and alteplase, with respect to groups of 10 mg/kg administration, the infarction area percentage is shown in FIG. 1, and the neurological symptom score is shown in FIG. 2 (*: P<0.05, **: P<0.01, ##: P<0.01), wherein t-PA in the Figures stands for alteplase (hereinafter the same shall apply).

TABLE 7

| | Infarction area [%] | | | | Neurological scores | | | |
|---|---|---|---|---|---|---|---|---|
| Sham | 2.9 ± 0.2 | | | | 0 ± 0 | | | |
| Control | 14.9 ± 3.08 | | | | 3.33 ± 0.67 | | | |
| | Initiation time of administration | | | | Initiation time of administration | | | |
| | 0 hr | 1 hr | 3 hr | 6 hr | 0 hr | 1 hr | 3 hr | 6 hr |
| SMTP-7 (1 mg/kg) | — | 11.4 ± 2.69 | — | — | — | 2.67 ± 0.33 | | — |
| SMTP-7 (10 mg/kg) | — | 7.01 ± 0.56** | 5.90 ± 0.36** | 7.93 ± 1.64** | — | 1.50 ± 0.67* | 1.67 ± 0.61* | 2.00 ± 0.45 |
| alteplase (0.01 mg/kg) | — | 11.2 ± 2.74 | — | — | — | 2.67 ± 0.56 | — | — |
| alteplase (0.1 mg/kg) | — | 9.67 ± 2.35 | — | — | — | 2.00 ± 0.77 | — | — |
| alteplase (10 mg/kg) | — | 5.43 ± 1.33## | 11.0 ± 3.61 | 13.8 ± 2.40 | — | 0.17 ± 0.17## | 1.33 ± 0.67## | 3.17 ± 0.48 |
| edaravone (1 mg/kg) | — | 12.8 ± 2.87 | — | — | — | 3.17 ± 0.17 | — | — |
| edaravone (3 mg/kg) | 9.95 ± 3.22 | 8.29 ± 1.61* | 12.3 ± 5.59 | — | 1.50 ± 0.67* | 1.50 ± 0.67* | 2.50 ± 0.56 | — |
| edaravone (10 mg/kg) | — | 9.29 ± 2.17 | — | — | — | 1.83 ± 0.65 | — | — |
| argatroban (1 mg/kg) | 10.0 ± 2.66 | 12.1 ± 2.46 | — | — | 2.33 ± 0.61 | 2.50 ± 0.50 | — | — |
| argatroban (10 mg/kg) | — | 11.5 ± 2.57 | — | — | — | 2.50 ± 0.56 | — | — |
| ticlopidine HCl (1 mg/kg) | 8.83 ± 1.73 | 13.1 ± 3.89 | — | — | 2.33 ± 0.42 | 2.67 ± 0.56 | — | — |

TABLE 7-continued

| | | | | | | | | |
|---|---|---|---|---|---|---|---|---|
| ticlopidine HCl (10 mg/kg) | — | 9.84 ± 1.81 | — | — | — | 2.33 ± 0.42 | — | — |

Numerical expression represents: mean ± SE (n = 6)

Sham: Group of sham treatment for generating cerebral infarction

*P < 0.05;

**P < 0.01 (The values of the control and the values of the groups of SMTP-7 (10 mg/kg) administration, and the values of the control and the values of the groups of edaravone (3 mg/kg) administration were compared by ANOVA and thereafter by Bonferroni test.)

#P < 0.05;

P < 0.01 (The values of the control and the values of the groups of alteplase (10 mg/kg) administration were compared by ANOVA and thereafter by Bonferroni test.)

When SMTP-7 was administered 1 hour after the initiation of ischemia, dose dependent improvement of the infarction area percentage and the neurological symptom was recognized. In the group of 10 mg/kg administration, for both of the infarction area percentage and the neurological symptom, significant improvement compared to the control group was recognized.

With respect to the infarction area percentage in the SMTP-7 (10 mg/kg) administration group, there was statistically significant improvement compared to the control group, even if the administration initiation time was delayed after the initiation of ischemia (administrations were initiated 1 hour, 3 hours, and 6 hours after the initiation of ischemia). The improvement rate of the group, for which the administration was initiated 1 hour after the initiation of ischemia, was 65.7% showing effectiveness nearly equivalent to the case of administration of alteplase, whose improvement rate was 78.9%.

With respect to the neurological symptom score of the SMTP-7 (10 mg/kg) administration groups, for which the administration was initiated 1 hour after or 3 hours after the initiation of ischemia, there was not remarkable improvement compared to the alteplase (10 mg/kg) administration group, but statistically significant improvement compared to the control group was recognized. In the SMTP-7 (10 mg/kg) administration group, for which the administrations was initiated 6 hours after the initiation of ischemia, there was no statistically significant improvement recognized, but some improving tendency was recognized.

When alteplase was administered 1 hour after the initiation of ischemia, dose dependent improvement of the infarction area percentage and the neurological symptom was recognized. In the group of 10 mg/kg administration, for both of the infarction area percentage and the neurological symptom, significant differences compared to the control group were recognized.

Among the alteplase (10 mg/kg) administration groups, significant improvement in the infarction area percentage compared to the control group was recognized in the case of the administration 1 hour after the initiation of ischemia. In the case of the administration 3 hours after the initiation of ischemia, some improving tendency was recognized, but there was no significant improvement compared to the control group recognized. In the case of the administration 6 hours after the initiation of ischemia, there was no statistically significant difference compared to the control group.

With respect to the neurological symptom score of the alteplase (10 mg/kg) administration groups, for which the administration was initiated 1 hour after or 3 hours after the initiation of ischemia, there was significant improvement compared to the control group recognized. In the case of the administration 6 hours after the initiation of ischemia, however, there was no statistically significant difference compared to the control group.

When edaravone was administered 1 hour after the initiation of ischemia, dose dependent improvement of the infarction area percentage and the neurological symptom was recognized. In the group of 3 mg/kg administration, for both of the infarction area percentage and the neurological symptom, significant improvement compared to the control group was recognized. By increasing the dose to 10 mg/kg, no further improvement of the effectiveness was recognized and the same level was maintained.

Among the edaravone (3 mg/kg) administration groups, improving tendency was recognized in the case of the administration 0 hour or 1 hour after the initiation of ischemia. No improvement was recognized in the case of the administration 3 hours after the initiation of ischemia.

With respect to the neurological symptom score among the edaravone (3 mg/kg) administration groups, significant improvement was recognized in the case of the administration 0 hour or 1 hour after the initiation of ischemia. No significant improvement was recognized in the case of the administration 3 hours after the initiation of ischemia.

Example 3

Comparison of Effectiveness Between SMTP-7 and Alteplase on Mouse Cerebral Infarction Model The improvement effectiveness of SMTP-7 and alteplase on the infarction area percentage, the neurological symptom and the edema percentage was compared using the mouse cerebral infarction model. At the same time the dose dependence of the degree of improvement of SMTP-7 was investigated.

SMTP-7 and alteplase were prepared as in Example 2. Ten mg/kg each was administered into the femoral vein 1 hour or 3 hours after the initiation of ischemia in a mouse cerebral infarction model, wherein 10% was administered by a bolus administration, and the rest by continuous administration over 30 min. Further, 0.1 mg/kg or 1 mg/kg of SMTP-7 was administered into the femoral vein 1 hour after the initiation of ischemia in a mouse cerebral infarction model, wherein 10% was administered by a bolus administration, and the rest by continuous administration over 30 min. Six mice were used for each condition.

Twenty four hours after the initiation of the operation neurological symptom of each mouse was examined to rate the neurological symptom. Then the brain of each mouse was extirpated and the infarction area was measured and the infarction area percentage was determined. The edema percentage was determined according to the following formula:

Edema percentage (%)=(Volume of the cerebral hemisphere affected by ischemia−Volume of the other side cerebral hemisphere)/Volume of the other side cerebral hemisphere×100

Figure 3:
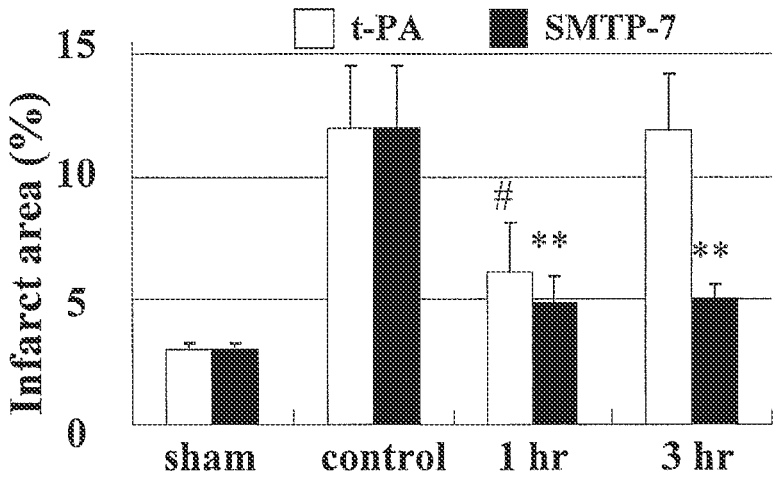
FIG. 3 is a diagram showing the percentage of a cerebral infarction area in Example 3 according to the present invention.
Figure 4:
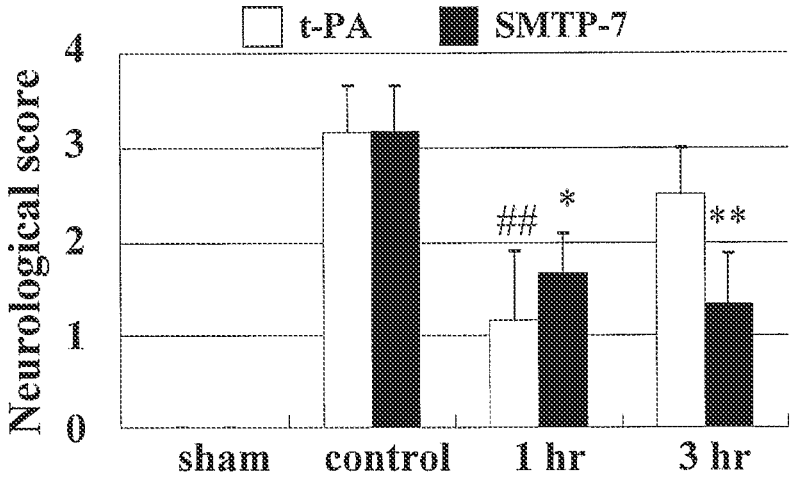
FIG. 4 is a diagram showing the neurological symptom in Example 3 according to the present invention.
Figure 5:
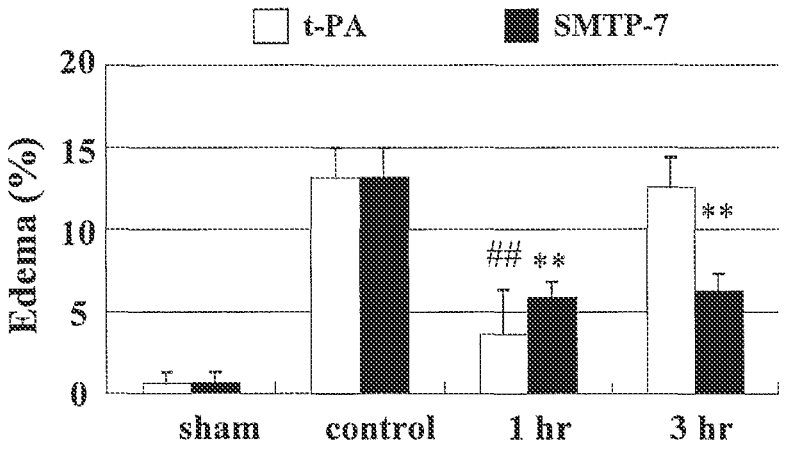
FIG. 5 is a diagram showing the edema percentage in Example 3 according to the present invention.

The evaluation results for SMTP-7 and alteplase at the dose of 10 mg/kg are shown in Table 8. The infarction area percentage of the same is shown in FIG. 3, the neurological symptom score is shown in FIG. 4, and the edema percentage is shown in FIG. 5. (*, P<0.05; **, P<0.01; #, P<0.05; ##, P<0.01)

Evaluation results of SMTP-7 at different doses are shown in Table 9.

TABLE 8

| | Infarction area [%] | | Neurological scores | | Edema percentage [%] | |
|---|---|---|---|---|---|---|
| Sham | 2.99 ± 0.27 | | 0 ± 0 | | 0.568 ± 0.796 | |
| Control | 11.9 ± 2.54 | | 3.17 ± 0.477 | | 13.2 ± 1.76 | |
| | Initiation time of administration | | Initiation time of administration | | Initiation time of administration | |
| | 1 hr | 3 hr | 1 hr | 3 hr | 1 hr | 3 hr |
| SMTP-7 | 4.87 ± 1.06** | 5.05 ± 0.576** | 1.67 ± 0.422* | 1.33 ± 0.558** | 5.81 ± 0.967** | 6.23 ± 1.07** |
| alteplase | 6.15 ± 1.94# | 11.9 ± 2.26 | 1.17 ± 0.749## | 2.50 ± 0.500 | 3.63 ± 2.67## | 12.6 ± 1.84 |

Numerical expression represents: mean ± SE (n = 6)

Sham: Group of sham treatment for generating cerebral infarction

*P < 0.05;

**P < 0.01 (The values of the control and the values of the groups of SMTP-7 administration were compared by ANOVA and thereafter by Bonferroni test.)

#P < 0.05;

P < 0.01 (The values of the control and the values of the groups of alteplase administration were compared by ANOVA and thereafter by Bonferroni test.)

Significant increase in the infarction area percentage was recognized in the control group compared to the sham group (Group of sham treatment for generating cerebral infarction).

Among the alteplase administration groups, significant improvement in the infarction area percentage compared to the control group was recognized in the group having initiated the administration 1 hour after the initiation of ischemia. In the group having initiated the administration 3 hours after the initiation of ischemia, no significant improvement compared to the control group was recognized.

Among the SMTP-7 (10 mg/kg) administration groups, significant improvement in the infarction area percentage compared to the control group was recognized in both of the group having initiated the administration after 1 hour, and the group having initiated the administration after 3 hours.

Significant increase in the neurological symptom score was recognized in the control group compared to the sham group (Group of sham treatment for generating cerebral infarction).

Among the alteplase administration groups, significant improvement in the neurological symptom score was recognized in the group having initiated the administration after 1 hour. In the group having initiated the administration after 3 hours, no significant improvement was recognized.

Among the SMTP-7 (10 mg/kg) administration groups, statistically significant improvement in the neurological symptom score compared to the control group was recognized in both of the group having initiated the administration after 1 hour, and the group having initiated the administration after 3 hours.

With respect to the edema percentage, among the alteplase administration groups, significant improvement was recognized in the group having initiated the administration after 1 hour, but no significant improvement was recognized in the group having initiated the administration after 3 hours.

Among the SMTP-7 (10 mg/kg) administration groups, significant improvement compared to the control group was recognized in both of the group having initiated the administration after 1 hour, and the group having initiated the administration after 3 hours.

TABLE 9

| | | Infarction area [%] | Neurological scores | Edema percentage [%] |
|---|---|---|---|---|
| Sham | | 2.99 ± 0.27 | 0 ± 0 | 0.568 ± 0.796 |
| Control | | 11.9 ± 2.54 | 3.17 ± 0.477 | 13.2 ± 1.76 |
| SMTP-7 | 0.1 mg/kg | 10.08 ± 2.07 | 2.5 ± 0.5 | 10.15 ± 1.817 |
| | 1 mg/kg | 6.66 ± 0.71* | 2 ± 0.632 | 8.81 ± 2.292 |
| | 10 mg/kg | 4.87 ± 1.06** | 1.67 ± 0.422* | 5.81 ± 0.967** |

Numerical expression represents: mean ± SE (n = 6)

Sham: Group of sham treatment for generating cerebral infarction

*P < 0.05;

**P < 0.01 (Comparison with the values of the control by ANOVA and thereafter by Bonferroni test.)

Significant improvement in any of the infarction area percentage, the neurological symptom score and the edema percentage was recognized compared to the control group in the SMTP-7 (10 mg/kg) administration group and the SMTP-7 (1 mg/kg) administration group.

Example 4

Comparison of Effectiveness Between SMTP-7 and Alteplase on Cerebral Blood Flow The improvement effectiveness of SMTP-7 and alteplase on the cerebral blood flow was compared using the mouse cerebral infarction model.

SMTP-7 and alteplase were prepared as in Example 2. SMTP-7 and alteplase were administered in an amount of 10 mg/kg into the femoral vein 1 hour after the initiation of ischemia in a mouse cerebral infarction model, wherein 10% was administered by a bolus administration, and the rest by continuous administration over 30 min. Three mice were used for each condition.

The cerebral blood flow was measured at 6 time points, namely before the initiation of ischemia, immediately after the initiation of ischemia, and after the completion of the drug administration 0 hour (immediately after the completion), 1 hour, 3 hours, and 24 hours.

The cerebral blood flow measurement was conducted by cutting the head skin of a mouse to expose the cranial bone, and measuring the blood flow of the whole brain surfaces by a laser-Doppler apparatus (moorFLPI, Moor Instruments Ltd, UK). The analysis was conducted using moorFLPI (Version 2.1) by rating percentage (%) relative to the value before the initiation of ischemia of each group. The results are shown in Table 10.

TABLE 10

| | Before initiation of ischemia | Immediately after initiation of ischemia | After completion of administration 0 hr | 1 hr | 3 hr | 24 hr |
|---|---|---|---|---|---|---|
| Control | 100% | 30.61 ± 2.22% | 45.08 ± 7.99% | 38.52 ± 2.92% | 31.97 ± 4.92% | 43.37 ± 7.51% |
| alteplase | 100% | 27.30 ± 2.35% | 56.45 ± 14.70% | 73.49 ± 20.33%* | 66.83 ± 11.10%* | 71.63 ± 6.06%* |
| SMTP-7 | 100% | 34.17 ± 5.22% | 43.74 ± 12.67% | 44.48 ± 12.59% | 48.90 ± 15.89% | 76.01 ± 9.71%* |

Numerical expression represents: mean ± SE (n = 3)

*P < 0.05 (Comparison with the values immediately after the initiation of ischemia by ANOVA and thereafter by Bonferroni test.)

In the SMTP-7 administration group the recovery of the cerebral blood flow was slower than the alteplase administration group, but 24 hours after the completion of the administration the cerebral blood flow recovered to the same level as the alteplase administration group. There was statistically significant difference compared to the control group.

Example 5

Study of Effectiveness of Triprenyl Phenol Compound on Mouse Cerebral Infarction Model Improving effectiveness on the mouse cerebral infarction model was studied using SMTP-6, SMTP-22, SMTP-25, SMTP-43, and SMTP-44D as triprenyl phenol compounds.

The used SMTP-6 was prepared identically as SMTP-7, except that L-tryptophan was used as an additive organic amino compound. The used SMTP-22 was prepared identically as SMTP-7, except that 4-aminosalicylic acid was used as an additive organic amino compound. The used SMTP-25 was prepared identically as SMTP-7, except that 3-aminosalicylic acid was used as an additive organic amino compound. The used SMTP-43 was prepared identically as SMTP-7, except that L-phenylglycine was used as an additive organic amino compound. The used SMTP-44D was prepared identically as SMTP-7, except that D-4-hydroxyphenylglycine was used as an additive organic amino compound. With these triprenyl phenol compounds 50 mg/mL solutions were prepared by adding 0.3 N NaOH and a physiological saline solution (0.9% NaCl) Thereafter, the solutions were adjusted to 10 mg/mL, and weak alkaline pH with 0.3 N HCl and a physiological saline solution, subjected to filtration sterilization, divided into small fractions, and cryopreserved at −30° C.

The cryopreserved triprenyl phenol compounds were dissolved at 1 mg/mL in a physiological saline solution just before a test. Ten mg/kg each was administered into the femoral vein 1 hour after the initiation of ischemia in a mouse cerebral infarction model, wherein 10% was administered by a bolus administration, and the rest by continuous administration over 30 min. Six mice were used for each condition.

Twenty four hours after the initiation of the operation, the infarction area percentage, the neurological symptom, and the edema percentage of each mouse were evaluated. The evaluation results are shown in Table 11. In Table 11, the evaluation results of the group, in which the administration of SMTP-7 (10 mg/kg) was initiated after 1 hour in Example 3, are also shown.

TABLE 11

| | Infarction area [%] | Neurological scores | Edema percentage [%] |
|---|---|---|---|
| Sham | 2.99 ± 0.27 | 0 ± 0 | 0.568 ± 0.796 |
| Control | 11.9 ± 2.54 | 3.17 ± 0.477 | 13.2 ± 1.76 |
| SMTP-7 | 4.87 ± 1.06** | 1.67 ± 0.422* | 5.81 ± 0.967** |
| SMTP-6 | 9.81 ± 1.43 | 3 ± 0.447 | 9.80 ± 2.74 |
| SMTP-22 | 4.37 ± 0.51** | 1.67 ± 0.422* | 4.55 ± 0.99** |
| SMTP-25 | 10.16 ± 1.04 | 2.5 ± 0.5 | 10.95 ± 2.57 |
| SMTP-43 | 5.70 ± 1.17** | 1.5 ± 0.5* | 3.28 ± 1.37** |
| SMTP-44D | 7.75 ± 2.71 | 2.17 ± 0.401 | 6.86 ± 2.92* |

Numerical expression represents: mean ± SE (n = 6)

Sham: Group of sham treatment for generating cerebral infarction

*P < 0.05;

**P < 0.01 (Comparison with the values of the control by ANOVA and thereafter by Bonferroni test.)

In the SMTP-22 administration group and the SMTP-43 administration group significant improvement in the infarction area percentage, the neurological symptom score and the edema percentage was recognized.

Example 6

Study of Parameter Change by Real Time Rt-PCR Method

Using the Mouse Cerebral Infarction model changes of parameters related to inflammation among the triprenyl phenol compound (10 mg/kg) administration groups, the alteplase (10 mg/kg) administration groups, and the alteplase (10 mg/kg) and aspirin (10 mg/kg) combined administration group were evaluated by a real time RT-PCR method. As the parameters IL-1β, TNF-α nd IL-6 were selected, which were typical parameters related to inflammation.

As triprenyl phenol compounds, SMTP-7, SMTP-6, SMTP-22, SMTP-25, SMTP-43 and SMTP-44D were used.

The triprenyl phenol compounds and alteplase were prepared same as in Example 2 and Example 5. Aspirin was dissolved at 1 mg/mL in a physiological saline solution.

The administrations of SMTP-7 (10 mg/kg) and alteplase (10 mg/kg) were initiated 1 hour or 3 hours after the initiation of ischemia. The administration method was same as Example 3.

The combined administration of alteplase (10 mg/kg) and aspirin (10 mg/kg) was initiated 3 hours after the initiation of ischemia. Alteplase was administered same as in Example 3, and aspirin was administered by a bolus intravenous injection into the femoral vein.

The administrations of SMTP-6, SMTP-22, SMTP-25, SMTP-43 and SMTP-44D were initiated 1 hour after the initiation of ischemia. The administration method was same as Example 5.

Six mice were used for each condition.

After 24 hours of the initiation of the operation, a Krebs-HEPES buffer was perfused from the heart and then the brain was extirpated.

After preparing brain slices, the fourth slice was divided to the left brain and the right brain, and homogenized respectively with 1 mL of TRIZOL (registered trademark) reagent (Invitrogen). After incubating at room temperature for 5 min, adding chloroform (0.2 mL), and mixing for 15 sec, incubation was carried out at room temperature for 3 min. The samples were centrifuged at 4° C. for 15 min at 12,000×g.

Since RNA moved to a water layer, the water layer was collected and, after addition of 0.5 mL of isopropyl alcohol, followed by incubation at room temperature for 10 min, centrifuged at 4° C. for 10 min at 12,000×g. Since a pellet was formed in a tube after the centrifugation, the supernatant was removed, and 1 mL of 75% ethanol was added followed by stirring to wash the pellet. The mixture was then centrifuged at 4° C. for 5 min at 7,500×g. After removing again the supernatant, being left for natural drying for 8 min, the pellet containing the RNA was dissolved in 100 μL of RNase-free water. cDNA was produced by reverse transcription of the RNA using a SuperScript (registered trademark) VILOTM cDNA Synthesis Kit (Invitrogen) by a Thermal Cycler 2720 (Applied Biosystems). More particularly, 4 μL of 5×VILOTM Reaction Mix, 2 μL of 10× SuperScript (registered trademark) Enzyme Mix, and 1 μg of each RNA were mixed and diluted to 20 μL with RNase-free water.

Reverse transcription was conducted using the above samples under the following conditions. After reacting at 25° C. for 10 min, at 42° C. for 60 min, and at 85° C. for 5 min, the product was stored at 4° C. With the cDNA as a template real time RT-PCR was carried out by ABI PRISM 7000 using SYBR (registered trademark) GreenERTM qPCR SuperMix for ABI PRISM (registered trademark; Invitrogen). More particularly, 12.5 μL of SYBR (registered trademark) GreenERTM qPCR SuperMix for ABI PRISM (registered trademark), 0.5 μL of a forward primer, 0.5 μL of reverse primer and 2.5 μL of the 20-fold diluted template were mixed and diluted to 25 μL with RNase-free water.

Real time RT-PCR was conducted using the above samples under the following conditions. After reacting at 50° C. for 2 min and at 95° C. for 15 min, a cycle of 94° C. for 15 sec, 55° C. for 30 sec, and 72° C. for 30 sec was repeated 40 times. Changes of the respective parameters were determined by a calibration curve method. β-actin was measured as an internal control, and the respective parameters were calculated as a relative value based on the β-actin. The results are shown in Table 12. The values in Table 12 are the ipsilesional values (the right brain).

The following primers were used:

```
β-actin forward:
                                        (SEQ. ID. NO: 1)
5'-CCTTCCTTCTTGGGTATGGAATC-3',

β-actin reverse:
                                        (SEQ. ID. NO: 2)
5'-TGCTAGGAGCCAGAGCAGTAATC-3',

IL-1β (Quiagen, QT01048355),

TNF-α (Quiagen, QT00104006),
and

IL-6 (Quiagen, QT00098875).
```

TABLE 12

| Relative value to β-actin | IL-1β | | TNF-α | | IL-6 | |
|---|---|---|---|---|---|---|
| Sham | 0.00358 ± 0.000676 | | 0.0102 ± 0.00334 | | 0.00235 ± 0.000457 | |
| Control | 0.116 ± 0.0428* | | 0.474 ± 0.191** | | 0.173 ± 0.0464* | |
| | Initiation time of administration | | Initiation time of administration | | Initiation time of administration | |
| | 1 hr | 3 hr | 1 hr | 3 hr | 1 hr | 3 hr |
| alteplase | 0.0408 ± 0.0173 | 0.347 ± 0.172**,## | 0.164 ± 0.0332## | 0.381 ± 0.155** | 0.0582 ± 0.0254 | 0.341 ± 0.138**,# |
| alteplase + Aspirin | — | 0.172 ± 0.0502 | — | 0.143 ± 0.0330## | — | 0.169 ± 0.0532* |
| SMTP-7 | 0.0314 ± 0.0171 | 0.0728 ± 0.0380 | 0.151 ± 0.0313## | 0.147 ± 0.0293## | 0.0356 ± 0.0138 | 0.0651 ± 0.0308 |
| SMTP-6 | 0.165 ± 0.0930 | — | 0.261 ± 0.119* | — | 0.220 ± 0.0850** | — |
| SMTP-22 | 0.040 ± 0.0140 | — | 0.087 ± 0.0295## | — | 0.071 ± 0.0437 | — |
| SMTP-25 | 0.060 ± 0.0249 | — | 0.049 ± 0.0158## | — | 0.0560 ± 0.0259 | — |
| SMTP-43 | 0.025 ± 0.0118 | — | 0.058 ± 0.0147## | — | 0.0234 ± 0.0115 | — |
| SMTP-44D | 0.070 ± 0.0435 | — | 0.081 ± 0.0304## | — | 0.0562 ± 0.0354 | — |

Numerical expression represents: mean ± SE (n = 6)

Sham: Group of sham treatment for generating cerebral infarction

*P < 0.05;

**P < 0.01 (Comparison with the values of Sham by ANOVA and thereafter by Bonferroni test.)

#P < 0.05;

P < 0.01 (Comparison with the values of the control by ANOVA and thereafter by Bonferroni test.)

TNF-α and IL-6 in the control group were increased significantly compared to the Sham group.

In the group, in which the administration of alteplase was initiated after 1 hour from the initiation of ischemia, no parameter was recognized, which showed remarkable increase compared to the Sham group, but in the group, in which the administration was initiated after 3 hours, significant increase in IL-1β, TNF-α and IL-6 compared to the Sham group was recognized. Among others, significant increase in IL-1β and IL-6 relevant to the control group was also recognized.

In the group administered with alteplase and aspirin in combination, the increase of IL-1β and TNF-α, which was obvious when alteplase was administered singly, was not recognized.

Among the SMTP-7 administration groups, not only in the group, in which the administration was initiated after 1 hour, but also in the group, in which the administration was initiated after 3 hours, remarkable increase in IL-1β, TNF-α and IL-6 was not recognized, namely SMTP-7 inhibited increase of such parameters.

In the SMTP-22 administration group, the SMTP-25 administration group, the SMTP-43 administration group, and the SMTP-44D administration group, remarkable increase in IL-1β, TNF-α and IL-6 was not recognized, namely SMTP-22, SMTP-25, SMTP-43, and SMTP-44D inhibited increase of such parameters.

In the SMTP-6 administration group, the increase in IL-1β, TNF-α and IL-6 was not inhibited.

Example 7

Study of Free Radical Scavenging Activity of Triprenyl Phenol Compound

To study the free radical scavenging activity of a triprenyl phenol compound, the following H-ORAC (hydrophilic oxygen radical absorbance capacity) assay, and modified H-ORAC (mH-ORAC) assay were conducted.

SMTP compounds evaluated by H-ORAC were used respectively in a form of a sodium salt aqueous solution, and the compounds evaluated by mH-ORAC were used respectively in a form of an acetone solution.

In H-ORAC a test compound was diluted appropriately with a buffer solution (75 mM phosphate buffer solution, pH 7.4) and used for measurement. In mH-ORAC a test compound was diluted appropriately by a 50% (v/v) acetone solution, prepared by diluting an acetone solution with water, to prepare a solution of 40-fold the final concentration. The solution was diluted 10-fold with a buffer solution for measurement (acetone final concentration 1.25%). As for the reference material Trolox, 500 μM/buffer solution was diluted appropriately with a buffer solution.

To a 96-well microplate (transparent, flat bottom, black wall) 50 μL of a test compound solution or a Trolox solution was placed, and additionally 100 μL of a fluorescein 140 nM/buffer solution as a fluorescent substance was added (final concentration 70 nM), followed by incubation at 37° C. for 10 mM.

As a free radical generator, 50 μL of a 48 mM/buffer solution of 2,2'-azobis(amidinopropane)dihydrochloride was added (final concentration 12 mM), and fluorescence intensity at fluorescence wavelength of 535 nm with excitation wavelength of 485 nm was measured at 2 min intervals for 90 min. The calibration curve was prepared between the Trolox final concentrations of 5 to 15 μM. The measurement was conducted by changing the concentration with n=3, and plotted on a diagram with time on the abscissa and the fluorescence intensity on the ordinate. Therewith evaluation was made using the value obtained by reducing the area under the curve for the blank from the area under the curve for the sample. The result was expressed as an equivalent to Trolox. The results are shown in Table 13, wherein TE stands for a Trolox equivalent.

TABLE 13

| | Measuring method | molTE/mol |
|---|---|---|
| SMTP-0 | mH-ORAC | 7.76 ± 0.36 |
| SMTP-1 | mH-ORAC | 4.35 ± 0.55 |
| SMTP-4 | H-ORAC | 1.79 ± 0.02 |
| SMTP-5D | H-ORAC | 1.71 ± 0.20 |
| SMTP-6 | H-ORAC | 3.73 ± 0.42 |
| SMTP-7 | H-ORAC | 2.08 ± 0.13 |
| SMTP-7 | mH-ORAC | 1.82 ± 0.27 |
| SMTP-8 | mH-ORAC | 1.69 ± 0.14 |
| SMTP-11 | H-ORAC | 2.52 ± 0.12 |
| SMTP-12 | H-ORAC | 3.18 ± 0.13 |
| SMTP-13 | H-ORAC | 3.07 ± 0.51 |
| SMTP-14 | H-ORAC | 4.43 ± 0.49 |
| SMTP-18 | mH-ORAC | 7.34 ± 0.22 |
| SMTP-19 | H-ORAC | 1.36 ± 0.05 |
| SMTP-20 | H-ORAC | 1.80 ± 0.46 |
| SMTP-21 | H-ORAC | 3.57 ± 0.13 |
| SMTP-22 | H-ORAC | 3.63 ± 0.15 |
| SMTP-23 | H-ORAC | 6.34 ± 0.37 |
| SMTP-24 | H-ORAC | 3.95 ± 0.13 |
| SMTP-25 | H-ORAC | 5.03 ± 0.72 |
| SMTP-26 | mH-ORAC | 2.05 ± 0.27 |
| SMTP-27 | H-ORAC | 5.01 ± 0.27 |
| SMTP-28 | H-ORAC | 6.89 ± 0.03 |
| SMTP-29 | H-ORAC | 5.60 ± 0.08 |
| SMTP-36 | H-ORAC | 3.61 ± 0.04 |
| SMTP-37 | H-ORAC | 4.09 ± 0.07 |
| SMTP-42 | H-ORAC | 3.28 ± 0.25 |
| SMTP-43 | H-ORAC | 2.74 ± 0.26 |
| SMTP-43D | H-ORAC | 2.32 ± 0.12 |
| SMTP-44 | H-ORAC | 4.84 ± 0.43 |
| SMTP-44D | H-ORAC | 5.56 ± 0.18 |
| SMTP-46 | H-ORAC | 3.19 ± 0.13 |
| SMTP-47 | H-ORAC | 2.13 ± 0.22 |

Meanwhile, just as a reference value, the ORAC value for α-tocopherol measured by an ORAC assay same as the above was 0.50 ± 0.02 by Trolox equivalent (Huang et al., J. Agric. Food Chem., 50, 1815-1821 (2002)).

As obvious from Table 13, all of the SMTP compounds according to the present invention have free radical scavenging activity equivalent to or higher than Trolox. Consequently, it is clear that the SMTP compounds according to the present invention have high antioxidative activity.

Example 8

Study of Plasmin Activity by Fibrinogen Zymography Method

The quantity of plasmin/$\alpha_2$-antiplasmin in plasma was measured by a fibrinogen zymography method for evaluating the plasmin activity, when a triprenyl phenol compound was administered to a mouse cerebral infarction model. As triprenyl phenol compounds, SMTP-7, SMTP-6, SMTP-22, SMTP-25, SMTP-43, and SMTP-44D were used.

The triprenyl phenol compounds were prepared same as in Example 2 and Example 5. The administration of 10 mg/kg of a triprenyl phenol compound was initiated 1 hour after the initiation of ischemia. The administration method was same as Example 3. Six mice were used for each condition.

A blood sample was taken according to the following method at 3 time points, namely after the completion of the administration 0 hour (immediately after the completion), 1 hour, and 3 hours. Under anesthesia with 1 to 1.5% isoflurane, the tail was cut in and 90 μL of blood was withdrawn from the abdominal vena cava into a syringe containing 10 μL of sodium citrate (3.8%) (sodium citrate:blood=1:9, final concentration of sodium citrate 0.38%).

After collection the blood was centrifuged (5000 rpm, 15 min, 4° C.) to separate plasma. A part of the plasma was mixed with equal quantity of a sample buffer (125 mM Tris-HCl (pH 6.8), 4% (w/v) SDS, 0.04% (w/v) bromophenol blue, 20% (w/v) sucrose), which was then divided into small fractions, and cryopreserved.

A part of the plasma was reserved and diluted 300-fold with 0.1 N NaOH and the protein content was determined by the Bradford method in order to even out the protein mass to be applied to an electrophoresis gel.

As the standard sample, a sample was prepared by reacting 10 μL of 120 nM plasmin (by SIGMA) and 10 μL of 600 nM $\alpha_2$-antiplasmin (by Wako Pure Chemical Industries, Ltd.) at 37° C. for 30 min, and mixing the same with 20 μL of the sample buffer.

An electrophoresis gel was prepared by overlaying a stacking gel on a 7.5% running gel containing 2 mg/mL fibrinogen (by SIGMA). Based on the determined protein mass, 3 to 15 μL of the sample was applied, so that the equal amount of protein was applied.

After electrophoresis at 10 mA/sheet, for 3 hours the stacking gel was removed and rinsed for 30 min twice with about 100 mL/gel of a rinse liquid (2.5% Triton X-100). After rinsing, incubation was carried out at 37° C. for 24 to 60 hours under gentle shaking with about 100 mL/sheet of an incubation buffer (0.1 M glycine-50 mM Tris-HCl, pH 8.3 at 37° C.).

Thereafter the gel was stained by a stain solution (0.075% CBB 8250, 22.5% methanol, 2.25% sulfosalicylic acid dihydrate, 7.5% trichloroacetic acid) at room temperature for 15 to 30 min with gentle shaking. Removing the stain solution, the gel was decolored by a decoloring solution (methanol: acetic acid:water=1:1:6), which was replaced with water at an appropriate time point according to appearance of bands observed.

The image on the gel was read in by an imaging analyzer (Printgraph (AE-6933FXCF), by ATTO) and the band intensity was evaluated. The results are expressed as a ratio to the value of the control group at 0 hour after the completion of the administration (immediately after the completion). The results are shown in Table 14.

TABLE 14

| | After completion of administration | | |
|---|---|---|---|
| | 0 hr | 1 hr | 3 hr |
| Control | 1 ± 0.26 | 1.01 ± 0.27 | 0.99 ± 0.23 |
| SMTP-7 | 1.49 ± 0.13 | 3.23 ± 0.47** | 3.27 ± 0.67** |
| SMTP-6 | 1.08 ± 0.12 | 1.17 ± 0.14 | 1.68 ± 0.10 |
| SMTP-22 | 1.79 ± 0.21* | 2.08 ± 0.33* | 1.99 ± 0.78 |
| SMTP-25 | 2.44 ± 0.28** | 2.68 ± 0.33** | 2.98 ± 0.60** |
| SMTP-43 | 2.64 ± 0.56** | 3.04 ± 0.47** | 3.18 ± 0.78** |
| SMTP-44D | 0.53 ± 0.11 | 0.66 ± 0.10 | 0.75 ± 0.22 |

Numerical expression represents: mean ± SE (n = 6)

*P < 0.05;

**P < 0.01 (Comparison with the values of the control of the same administration time by ANOVA and thereafter by Bonferroni test.)

Among the SMTP-7 administration groups, in case of 1 hour after the completion of the administration significant increase of the plasmin activity was recognized and similar activity was maintained in case of 3 hours after the completion of the administration.

Among the SMTP-22 administration groups, the SMTP-25 administration groups, and the SMTP-43 administration groups, even in the case immediately after the completion significant increase of the plasmin activity was recognized and similar activity was maintained in cases of 1 hour and 3 hours after the completion of the administration.

Among the SMTP-6 administration groups, and the SMTP-44D administration groups, no significant increase of the plasmin activity was recognized.

Example 9

Study of Therapeutic Effect of SMTP-7 in Crab-Eating Monkey Cerebral Infarction Model A reducing effect of a cerebral infarction size and an improving effect of a neurological symptom of SMTP-7 in a crab-eating monkey cerebral infarction model were studied according to the following testing method.

[Constitution of Groups]

Medium group: physiological saline solution, 2 to 3 year old male crab-eating monkeys, 6 monkeys SMTP-7 administration group: 10 mg/kg, 2 to 3 year old male crab-eating monkeys, 6 monkeys

[Environmental Conditions of Animal Room]

Cage: stainless steel cage, W×D×H=600×600×800 (mm)

Cage floor size: 0.36 $m^2$

Temperature (allowable range): 20 to 26° C.

Humidity (allowable range): 40 to 70%

Lighting hours (setup): 12 hours/day (7:00 to 19:00)

Poundage condition: individual housing

[Feed]

Kind: solid feed LabDiet (by PMI Nutrition International)

Feeding method: daily 100 g

[Drinking Water]

Kind: tap water

Water feeding method: free-feeding by a 500 mL water bottle

[Administration of Test Substance]

Administration route of test substance: intravenous administration

Test substance dose: 10 mg/kg

Administration method of test substance: The administration volume was set at 10 mL/kg. A Surflo indwelling needle was indwelled in the left saphenous vein, 1 mg/kg (1 mL/kg) was administered 1 hour after ischemia as a bolus over 5 sec, then 9 mg/kg (9 mL/kg) was administered continuously over 30 min using a syringe pump.

Preparation of administration liquid: SMTP-7 was dissolved in a physiological saline solution at 1 mg/mL. More particularly, to 70.0 mg of a SMTP-7 sodium salt (containing 63.1 mg of SMTP-7) was added 63.1 mL of a physiological saline solution, and the liquid was stirred by a magnetic stirrer under heating in a hot-water bath (37° C.) for dissolution. An ultrasonic treatment was conducted according to need. After dissolution the liquid was subjected to filter sterilization by a sterile filter (0.22 μm, made of cellulose acetate). The administration liquid was prepared before using. After the preparation it was kept in a 37° C. hot-water bath until immediately before the use, and the administration was finished within 4 hours after the preparation.

[Treatment of Cerebral Infarction]

Animal anesthesia was conducted according to the standard experimental protocol (SPHPR400-3A). More particularly, anesthesia was induced by intramuscular administration of ketamine (Daiichi Sankyo Propharma Co. Ltd.) (10 mg/kg)+atropine (Mitsubishi Tanabe Pharma Corp.) (0.05 mg/kg). Thereafter, conducting tracheal intubation, the animal was fixed to an operating table under inhalation anesthesia with isoflurane (Abbott).

The treatment of cerebral infarction was conducted according to the standard experimental protocol (SPHPR710-15A). More particularly, after extirpating the right eyeball, the eyeground bone outside the optic nerve exit was removed by a dental drill to expose the dura mater. The dura mater was carefully detached to identify the middle cerebral artery. The origin part of the middle cerebral artery was separated from the arachnoid mater and a light irradiation probe for generating a thrombus was fixed on the middle cerebral artery. At the distal end of the probe a probe of a pulse Doppler blood flowmeter (Crystal Bio, PDV-20) was placed. An intravenous administration of rose bengal (Wako Pure Chemical Industries, Ltd.) (20 mg/kg) over 6 min was initiated and an irradiation with green light with the wavelength of 540 nm (1.40 million LUX) was conducted for 20 min to block the middle cerebral artery by a thrombus. The initiation time of the light irradiation and the administration of the rose Bengal was defined as the initiation time of ischemia. The middle cerebral artery blood flow was measured by the pulse Doppler blood flowmeter continuously for 2 hours from the initiation time of the light irradiation and then the incision was closed. A series of procedures were carried out completely under an operating microscope to minimize intraoperative hemorrhage to the utmost. Further, the rectal temperature of an animal under operation was monitored, and the animal was kept warmed by a heating pad, so as to maintain the body temperature of the animal in a physiological range (37.0 to 38.5° C.).

[Postoperative Management]

An intramuscular administration of penicillin G (Meiji Seika Pharma, Limited) (100,000 Unit/head/day) was carried out as a preventive measure against infection and an analgesic treatment by means of an administration of 0.02 mg/head of buprenorphine hydrochloride (Lepetan, Otsuka Pharmaceutical Co., Ltd.).

[Evaluation Method of Neurological Symptom]

Neurological symptoms as described below were observed 24 hours after ischemia according to J. Neurosci. Meth., 2001; 105: 45-53.

Rating of a neurological symptom score:

(1) Consciousness

Active movement, same as normal animal (0)

Arousal state, aggressive (4)

Arousal state, able to escape (6)

Arousal state, but slow to react (8)

Drowsiness (mild), reactive to stimulation (10)

Drowsiness (severe), eye is opened by strong stimulation (16)

Loss of sensation, reactive to persistent stimulation (20)

Coma (mild), reflex movement only (24)

Coma (severe), motionless (28)

(2) Sensory system

Sense of face (ipsilesional/contralesional)

Normal reaction to facial stimulation (0/0)

No normal reaction to facial stimulation (3/3)

Reaction of auricular (ipsilesional/contralesional)

Reactive when ear is pulled (0/0)

Not reactive when ear is pulled (3/3)

Painful stimulation (inferior limb, ipsilesional/contralesional)

When toe is nipped, it is quickly drawn away (0/0)

When toe is nipped, it is slowly drawn away (3/3)

When toe is nipped, it is not drawn away (5/5)

(3) Motor system

Hand (ability to grip/move, ipsilesional/contralesional)

Normal (0/0)

Decrease in gripping force/disharmonious movement (2/2)

Paralyzed, unable to grip (4/4)

Leg/foot (ability to grip/move, ipsilesional/contralesional)

Normal (0/0)

Able to bend and lift knee (2/2)

Able to move but unable to lift (4/4)

Paralyzed, unable to move (6/6)

Upper arm muscle tone (ipsilesional/contralesional)

Normal (0/0)

Obvious muscle relaxation (spastic) (3/3)

Inferior limb muscle tone (ipsilesional/contralesional)

Normal (0/0)

Obvious muscle relaxation (spastic) (3/3)

(4) Skeletal muscle coordination system

Normal, able to walk (0)

Failure of muscular coordination (mild), disturbance in walking (4)

Failure of muscular coordination, unable to climb to a roost (6)

Able to stand up spontaneously, difficult to walk (10)

Sit down position on floor, circling movement by stimulation (12)

Side-lying position on floor (16)

Motionless (18)

[Collection of Brain Specimen]

After the neurological symptom observation 24 hours after the operation, a euthanasia treatment was conducted by means of a megadose of pentobarbital and the brain was extirpated. Six mm-thick coronal slices were prepared and photographed for quantitative determination of a hemorrhagic infarction. Thereafter, the infarction area was stained in a 2% TTC solution and photographs were taken for quantitative determination of an infarction size. For evaluations of the hemorrhagic infarction and the infarction area, the occipital lobe side of each slice was used.

[Analysis Method]

Photographs of an individual were converted to TIF images and hemorrhagic infarction areas and the respective infarction areas were marked by Photoshop 7.0 (Adobe), which sizes were then measured by Scion Image 0.4.0.3 (Scion Corporation).

As a hemorrhagic infarction area the sum of area sizes of the respective cross-sections was used.

An infarction area was measured for cerebral cortex, white matter, and basal ganglion separately with respect to each cross-section, and the infarction volume ($mm^3$) was calculated by multiplying the thickness (6 mm) of the slice.

The experiment result data were tabulated and graphed by Microsoft Excel (Version 2003, Microsoft Inc.) and expressed in mean±standard deviation (S.D.).

Statistical analysis was conducted using Microsoft Excel (Version 2003, Microsoft Inc.), and an unpaired t-test (equal variances) was carried out between the medium group and the SMTP-7 administration group to judge that significant difference was present if $P<0.05$.

[Results of Blood Flow Measurement]

Time to Occlusion and Total Occlusion Time are shown in Table 15. With respect to Time to Occlusion and Total Occlusion Time, no significant difference was recognized between the medium group and the SMTP-7 administration group.

Since the administration of the medium and SMTP-7 was initiated 60 min after ischemia, the Total Occlusion Time was divided into the Occlusion Time from the initiation of the ischemia to 60 min after the same, and the Occlusion Time from 60 min after the same to 120 min after the same, and analyzed respectively. As shown in Table 16, no significant reducing action on the occlusion time was recognized.

TABLE 15

| Treatment | Time to Occlusion (min) | Total Occlusion Time (min) |
|---|---|---|
| Medium group | 6.9 ± 2.8 | 103.3 ± 6.5 |
| SMTP-7 administration group | 6.9 ± 2.5 | 86.8 ± 18.8 |

TABLE 16

| Treatment | Occlusion Time (min) | |
|---|---|---|
| | 0~60 min | 60~120 min |
| Medium group | 46.3 ± 4.9 | 57.0 ± 2.3 |
| SMTP-7 administration group | 45.5 ± 3.8 | 41.3 ± 18.9 |

[Observation Results of Neurological Symptom]

The observation results of a neurological symptom 24 hours after ischemia are shown in the following Table 17. In the SMTP-7 administration group significant neurological symptom improving action (P<0.05) was recognized in the sensory system and the skeletal muscle coordination system. Further, significant neurological symptom improving action (P<0.05) was recognized also in the total score.

TABLE 17

| Treatment | Consciousness | Sensory system | Motor system | Skeletal muscle coordination system | Total |
|---|---|---|---|---|---|
| Medium group | 10.3 ± 3.2 | 9.7 ± 1.0 | 13.7 ± 2.7 | 10.0 ± 3.1 | 43.7 ± 8.1 |
| SMTP-7 administration group | 7.7 ± 2.0 | 7.5 ± 1.6* | 10.7 ± 2.7 | 5.3 ± 2.4* | 31.2 ± 7.9* |

*P < 0.05 vs. medium group

[Measurement Results of Infarction Size]

The measurement results of the hemorrhagic infarction area size and the cerebral infarction size 24 hours after ischemia are shown in the following Table 18 and Table 19. In the SMTP-7 administration group, significant reduction (P<0.05) about the hemorrhagic infarction was recognized. Further, by the SMTP-7 administration, significant reduction (P<0.05) in the infarction size of the basal ganglion, and significant reduction (P<0.05) in the whole infarction size were recognized.

TABLE 18

| Treatment | Hemorrhagic infarction area size ($mm^2$) |
|---|---|
| Medium group | 29.0 ± 9.6 |
| SMTP-7 administration group | 14.1 ± 7.4 (P < 0.05) |

TABLE 19

| Treatment | Total | Cerebral cortex | Basal ganglion | White matter |
|---|---|---|---|---|
| Medium group | 3358.2 ± 1299.3 | 877.7 ± 1081.3 | 2291.2 ± 379.7 | 189.3 ± 105.8 |
| SMTP-7 administration group | 1745.1 ± 749.5* | 237.8 ± 198.8 | 1419.7 ± 633.8* | 87.7 ± 71.8 |

Unit: $mm^3$,

*P < 0.05 vs. medium group

From the above it has become clear that significant reducing action of the infarction size 24 hours after ischemia was exhibited in a crab-eating monkey thrombotic middle cerebral artery occlusion model as the result of the administration of SMTP-7 (10 mg/kg) 1 hour after ischemia. According to this result, a significant improving action of a neurological symptom and a significant reducing action of a hemorrhagic infarction were indicated.

Although the cerebral infarction area reducing action of SMTP-7 is believed to be attributable to the thrombolytic action of the same, there was no influence on the occlusion time of the middle cerebral artery according to the above study results. A reason for this may be attributable to a short measurement time of the blood flow after the SMTP-7 administration. SMTP-7 reduced significantly the infarction size of the basal ganglion including a striate body as a main part. The striate body is the site most vulnerable to ischemia and is a region depending on the blood flow of the perforating artery from the origin part of the middle cerebral artery. While, the blood flow measuring point was at a distal part of the middle cerebral artery, and SMTP-7 should have lysed gradually a thrombus from the origin part of the middle cerebral artery occluded by the thrombus, thus presumably resulting in remarkable reduction in the infarction size of the basal ganglion.

The results of Examples 1 to 9 can be summarized as follows.

As obvious from the results of Examples 2 and 3, it has been confirmed that SMTP-7 exhibits a suppressing action on the infarction area percentage and on the expression of a neurological symptom in a cerebral infarction model animal.

As obvious from the results of Example 4, it has been confirmed that SMTP-7 can gradually recover the cerebral blood flow after infarction in a cerebral infarction model animal. From this fact it can be presumed that with SMTP-7 the risk of causing ischemia reperfusion damage inherent to rapid recovery of the blood flow is limited.

As obvious from the results of Example 6, it has been confirmed that SMTP-7 exhibits an inhibitory action on increase in inflammation parameters of IL-1β, TNF-α, and IL-6 in a cerebral infarction model animal.

As obvious from the results of Example 7, it has been confirmed that SMTP-7 exhibits a strong scavenging action on a free radical, which is one of the damaging factors with respect to cell damaging caused by ischemia, and has an antioxidative activity.

As obvious from the results of Example 8, it has been confirmed that SMTP-7 exhibits an enhancing action on the plasmin activity in the blood.

As obvious from the results of Example 9, it has been confirmed that SMTP-7 exhibits a significant reducing action on the infarction size, and exhibits a significant improving action on a neurological symptom and a significant mitigating action on a hemorrhagic infarction, in a cerebral infarction model animal.

From the above, a composition containing SMTP-7 can be used as a cytoprotective agent having the effectiveness for inhibiting the dysfunction caused by ischemia.

As obvious from the results of Example 5, it has been confirmed that SMTP-22 and SMTP-43 exhibit a suppressing action on the infarction area percentage and on the expression of a neurological symptom in a cerebral infarction model animal.

As obvious from the results of Example 6, it has been confirmed that SMTP-22, SMTP-25, SMTP-43 and SMTP-44D exhibit an inhibitory action on increase in inflammation parameters of IL-1β, TNF-α, and IL-6 in a cerebral infarction model animal.

As obvious from the results of Example 7, it has been confirmed that SMTP-6, SMTP-22, SMTP-25, SMTP-43 and SMTP-44D exhibit a strong scavenging action on a free radical, which is one of the damaging factors with respect to cell damaging caused by ischemia, and have an antioxidative activity.

As obvious from the results of Example 8, it has been confirmed that SMTP-22, SMTP-25 and SMTP-43 exhibit an enhancing action on the plasmin activity in the blood.

With respect to SMTP-6, SMTP-25 and SMTP-44D, however, it has been not confirmed in Example 5 that they exhibit a suppressing action on the infarction area percentage and on the expression of a neurological symptom. On the other hand, it has been confirmed that SMTP-6 has a scavenging activity on a free radical. Further, it has been confirmed that SMTP-25 inhibits increase of an inflammation parameter, has scavenging activity on a free radical, and enhances the plasmin activity in the blood. It has been confirmed that SMTP-44D inhibits increase of an inflammation parameter, and has scavenging activity on a free radical.

It can be presumed that SMTP-6, SMTP-25 and SMTP-44D would exhibit a suppressing action on the infarction area percentage and on the expression of a neurological symptom, if the dose thereof to a model animal should be adjusted appropriately.

From the above, a composition containing any one selected out of SMTP-6, SMTP-22, SMTP-25, SMTP-43 and SMTP-44D can be used as a cytoprotective agent having the effectiveness for inhibiting the dysfunction caused by ischemia.

As obvious from the results of Example 7, it has been confirmed that SMTP-0, SMTP-1, SMTP-4, SMTP-5D, SMTP-8, SMTP-11 to 14, SMTP-18 to 21, SMTP-23, SMTP-24, SMTP-26 to 29, SMTP-36, SMTP-37, SMTP-42, SMTP-43D, SMTP-44, SMTP-46 and SMTP-47 exhibit a scavenging action as strong as, or stronger than Trolox, on a free radical, which is one of the damaging factors with respect to cell damaging caused by ischemia, and have an antioxidative activity.

From the above, a composition containing any one selected out of SMTP-0, SMTP-1, SMTP-4, SMTP-5D, SMTP-8, SMTP-11 to 14, SMTP-18 to 21, SMTP-23, SMTP-24, SMTP-26 to 29, SMTP-36, SMTP-37, SMTP-42, SMTP-43D, SMTP-44, SMTP-46 and SMTP-47 can be used as a cytoprotective agent having the effectiveness for inhibiting the dysfunction caused by ischemia.

Consequently, a composition containing a triprenyl phenol compound according to the present invention can be used as a cytoprotective agent having the effectiveness for inhibiting the dysfunction caused by ischemia.

Further, a composition containing a triprenyl phenol compound according to the present invention can be used for a method of treatment for ischemic damage including the administration of the composition to a patient affected by ischemic damage.

The entire disclosures of Japanese Patent Application No. 2009-160278 applied on Jun. 7, 2009 are hereby incorporated by reference.

All the literature, patent literature, and technical standards cited herein are also herein incorporated to the same extent as provided for specifically and severally with respect to an individual literature, patent literature, and technical standard to the effect that the same should be so incorporated by reference.

Sequence Listing

```
                    SEQUENCE LISTING

<160> NUMBER OF SEQ ID NOS: 2

<210> SEQ ID NO 1
<211> LENGTH: 23
<212> TYPE: DNA
<213> ORGANISM: Artificial
<220> FEATURE:
<223> OTHER INFORMATION: primer for b-actin

<400> SEQUENCE: 1

ccttccttct tgggtatgga atc                                    23


<210> SEQ ID NO 2
<211> LENGTH: 23
<212> TYPE: DNA
<213> ORGANISM: Artificial
<220> FEATURE:
<223> OTHER INFORMATION: b-actin R

<400> SEQUENCE: 2

tgctaggagc cagagcagta atc                                    23
```

The invention claimed is:

[1. A method of treatment of cerebral hemorrhagic infarction, comprising the step of administering a drug containing a triprenyl phenol of formula (II) or formula (III) to a patient affected by cerebral hemorrhagic infarction:

(II)

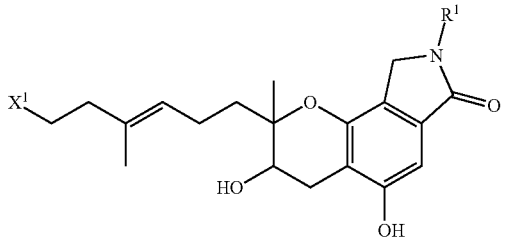

(III)

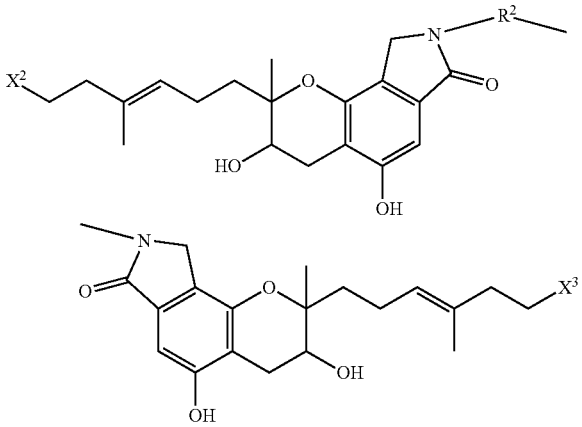

wherein $X^1$, $X^2$ and $X^3$ are each independently —CHY—$C(CH_3)_2Z$; Y and Z are each independently —H or —OH, or jointly form a bond, and $R^1$ is selected from among any one of the following (A) through (C):

(A) a residue of an amino compound selected from the group consisting of a natural amino acid, a D-isomer of a natural amino acid, and a compound derived by replacing a carboxy group in a natural amino acid, or a D-isomer of a natural amino acid, with a hydrogen atom, a hydroxy group, or a hydroxymethyl group, from which one amino group has been removed, with the proviso that $R^1$ is not hydroxymethyl;

(B) an aromatic group having at least one selected from the group consisting of a carboxy group, a hydroxy group, a sulfonic group and a secondary amino group as a substituent or a part of a substituent, or an aromatic group that contains a secondary amino group and may contain a nitrogen atom; and (C) an aromatic amino acid residue represented by the following formula (II-1)

(II-1)

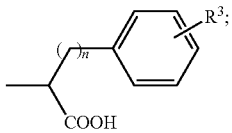

wherein, in formula (II-1), n is 0 or 1, and $R^3$ is at least one substituent selected from the group consisting of a hydroxy group, a carboxy group, and a C1 to C5 alkyl group, wherein $R^3$ may be present or absent; and wherein, in formula III, $R^2$ and the two nitrogens to which it is attached are derived from a diamine selected from the group consisting of: a natural amino acid with two amino groups; a D-isomer of a natural amino acid with two amino groups; a compound derived from a natural amino acid with two amino groups by replacing a carboxy group with a hydrogen atom, a hydroxy group, or a hydroxymethyl group; a compound derived from a D-isomer of a natural amino acid with two amino groups by replacing a carboxy group with a hydrogen atom, a hydroxy group, or a hydroxymethyl group; compounds having the formula $H_2N—CH(COOH)—(CH_2)_n—NH_2$ wherein n is an integer from 0 to 9; and compounds having the formula $H_2N—CH(COOH)—(CH_2)_m—S_p—(CH_2)_q—CH(COOH)—NH_2$ wherein m, p and q are each independently an integer from 0 to 9.]

[2. The method of treatment of cerebral hemorrhagic infarction according to claim 1, wherein the triprenyl phenol compound is SMTP-7.]

[3. The method of treatment of cerebral hemorrhagic infarction according to claim 1, wherein the patient is a patient with respect to whom treatment with a thrombolytic drug is contraindicated.]

[4. The method of treatment of cerebral hemorrhagic infarction according to claim 3, wherein the triprenyl phenol compound is SMTP-7.]

*5. A method for treating cerebral thrombosis in a human subject in need thereof, comprising administering a therapeutically effective amount of a compound represented by formula (III) to the human subject suffering from cerebral thrombosis, wherein use of a thrombolytic drug is contraindicated in the human subject:*

(III)

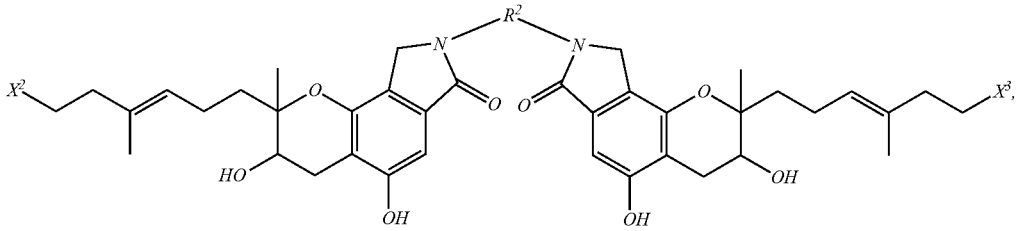

*wherein $X^2$ and $X^3$ are each —CHY—$C(CH_3)_2Z$; Y and Z jointly form a bond, and $R^2$ and the two nitrogens to which it is attached are derived from compounds having the formula $H_2N—CH(COOH)—(CH_2)_n—NH_2$ wherein n is 3.*

*6. A method for treating cerebral embolism in a human subject in need thereof, comprising administering: to a subject experiencing a cerebral embolism and having experienced at least one symptom of said cerebral embolism for three or more hours, a therapeutically effective amount of a compound represented by formula (III) to the human subject:*

(III)

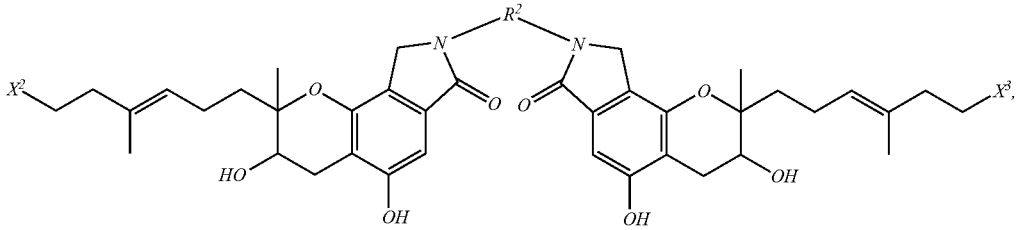

*wherein $X^2$ and $X^3$ are each —CHY—C($CH_3$)$_2$Z; Y and Z jointly form a bond, and $R^2$ and the two nitrogens to which it is attached are derived from compounds having the formula $H_2N$—CH(COOH)—($CH_2$)$_n$—$NH_2$ wherein n is 3.*

*7. A method for treating cerebral embolism in a human subject in need thereof, comprising administering: to a subject experiencing a cerebral embolism and having a contraindication for use of a thrombolytic drug, a therapeutically effective amount of a triprenyl phenol of formula (III) to the human subject:*

(III)

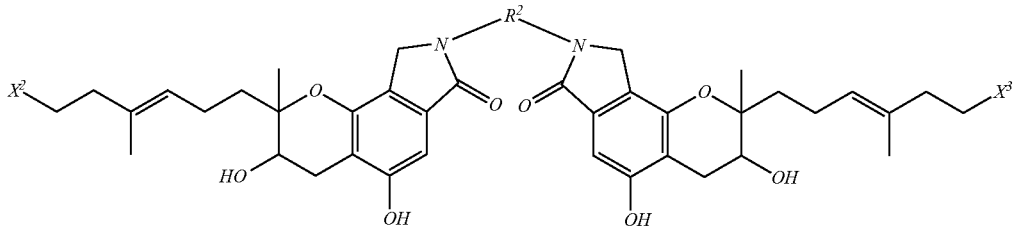

*wherein $X^2$ and $X^3$ are each independently —CHY —C($CH_3$)$_2$Z; Y and Z are each independently —H or —OH, or jointly form a bond, and*

*$R^2$ and the two nitrogens to which it is attached are derived from compounds having the formula $H_2N$—CH(COOH)—($CH_2$)$_n$—$NH_2$ wherein n is an integer from 0 to 9.*

*8. A method of reducing ischemia reperfusion damage in a human subject, wherein the human subject is suffering from cerebral thrombosis or cerebral embolism and having experienced at least one symptom of said cerebral thrombosis or cerebral embolism for three or more hours, said method comprising administering a therapeutically effective amount of a triprenyl phenol of formula (III) to the human subject:*

(III)

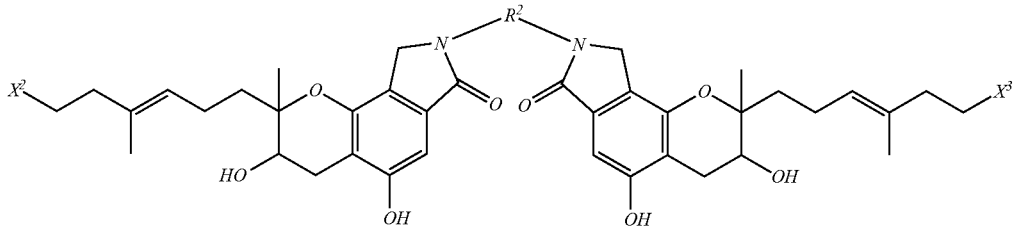

*wherein $X^2$ and $X^3$ are each independently —CHY —C($CH_3$)$_2$Z; Y and Z are each independently —H or —OH, or jointly form a bond, and*

*$R^2$ and the two nitrogens to which it is attached are derived from compounds having the formula $H_2N$—CH(COOH)—($CH_2$)$_n$—$NH_2$ wherein n is an integer from 0 to 9.*

*9. A method for treating cerebral thrombosis in a human subject in need thereof, comprising administering, to the subject suffering from cerebral thrombosis and having experienced at least one symptom of said cerebral thrombosis for three or more hours, a therapeutically effective amount of a triprenyl phenol of formula (III) to the human subject:*

(III)

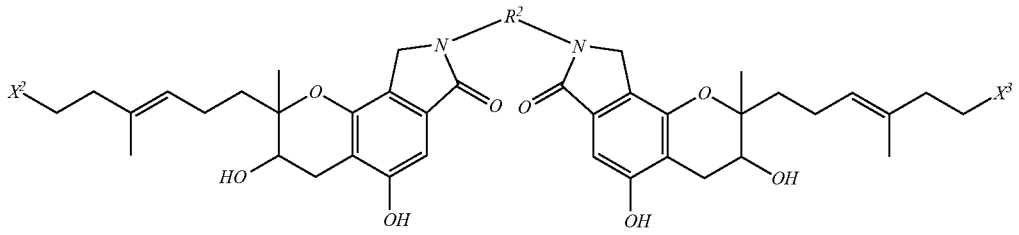

*wherein $X^2$ and $X^3$ are each independently —CHY—$C(CH_3)_2Z$; Y and Z are each independently —H or —OH, or jointly form a bond, and*

*$R^2$ and the two nitrogens to which it is attached are derived from compounds having the formula $H_2N$—CH(COOH)—$(CH_2)_n$—$NH_2$ wherein n is an integer from 0 to 9.*

*10. The method of claim 9, wherein said administering is carried out within 12 hours of onset of at least one symptom of cerebral thrombosis.*

*11. The method of claim 9, wherein said subject has discontinued thrombolytic drug treatment for cerebral thrombosis.*

*12. The method of claim 9, wherein said administering is carried out after the administration of a thrombolytic drug.*

*13. The method of claim 9, wherein no additional thrombolytic drug is administered to the subject in combination with the compound of formula (III).*

*14. The method of claim 7, wherein said triprenyl phenol of formula (III) has Y and Z jointly forming a bond and n is 3.*

*15. The method of claim 8, wherein said triprenyl phenol of formula (III) has Y and Z jointly forming a bond and n is 3.*

*16. The method of claim 9, wherein said triprenyl phenol of formula (III) has Y and Z jointly forming a bond and n is 3.*

* * * * *